(12) United States Patent
Lewis et al.

(10) Patent No.: US 7,964,610 B2
(45) Date of Patent: Jun. 21, 2011

(54) BUPRENORPHINE DERIVATIVES AND USES THEREOF

(75) Inventors: John William Lewis, Winscombe (GB); Christopher Bourne Chapleo, Hull (GB)

(73) Assignee: Reckitt Benckiser Healthcare (UK) Limited, Slough (GB)

( * ) Notice: Subject to any disclaimer, the term of this patent is extended or adjusted under 35 U.S.C. 154(b) by 478 days.

(21) Appl. No.: 12/294,462

(22) PCT Filed: Mar. 27, 2007

(86) PCT No.: PCT/GB2007/001120
§ 371 (c)(1),
(2), (4) Date: Sep. 25, 2008

(87) PCT Pub. No.: WO2007/110636
PCT Pub. Date: Oct. 4, 2007

(65) Prior Publication Data
US 2010/0234412 A1 Sep. 16, 2010

(30) Foreign Application Priority Data
Mar. 28, 2006 (GB) .................................. 0606124.6

(51) Int. Cl.
*A61K 31/4748* (2006.01)
*C07D 491/08* (2006.01)
(52) U.S. Cl. ......................................... 514/279; 546/39
(58) Field of Classification Search .................. 514/279; 546/39
See application file for complete search history.

(56) References Cited

U.S. PATENT DOCUMENTS

| | | | |
|---|---|---|---|
| 4,668,685 A | 5/1987 | Shami |
| 4,935,428 A | 6/1990 | Lewis |
| 5,750,534 A | 5/1998 | Yoa-Pu |
| 5,817,665 A | 10/1998 | Dante |
| 5,849,915 A | 12/1998 | Kim |
| 5,985,880 A | 11/1999 | Chang |
| 6,004,969 A | 12/1999 | Hu |
| 6,225,321 B1 | 5/2001 | Hu |
| 6,300,332 B1 | 10/2001 | Chang |
| 6,696,088 B2 | 2/2004 | Oshlack |
| 6,716,449 B2 | 4/2004 | Oshlack |
| 7,195,882 B2 | 3/2007 | Root |
| 7,220,842 B2 | 5/2007 | Zheng |
| 2004/0033253 A1 | 2/2004 | Shevchuk |
| 2004/0151670 A1 | 8/2004 | Blondino |
| 2005/0075361 A1 | 4/2005 | Wang |
| 2005/0085440 A1 | 4/2005 | Birch |
| 2005/0142072 A1 | 6/2005 | Birch |
| 2005/0152843 A1 | 7/2005 | Bartholomaus |
| 2005/0154002 A1 | 7/2005 | Crooks |
| 2005/0186139 A1 | 8/2005 | Bartholomaus |
| 2005/0191244 A1 | 9/2005 | Bartholomaus |
| 2005/0214223 A1 | 9/2005 | Bartholomaus |
| 2006/0287244 A1 | 12/2006 | Chandran |
| 2007/0140975 A1 | 6/2007 | Baichwal |

FOREIGN PATENT DOCUMENTS

| | | |
|---|---|---|
| EP | 1131059 | 11/1999 |
| EP | 1422230 | 11/2002 |
| EP | 1558221 | 10/2003 |

OTHER PUBLICATIONS

Imoto, "Transdermal Prodrug Concepts: Permeation of Buprenorphine and Its Alkyl Esters through Hairless Mouse Skin and Influence of Vehicles" *Biol. Pharm. Bull.* (1996), vol. 19, pp. 263-267.
Jasinski and Preston, "Laboratory Stuides of Buprenorphine in Opioid Abusers", Buprenorphine, Ed. A Cowan, JW Lewis, Wiley-Lis, (1995), pp. 189-211.
Stinchcomb, "A Solubility and Related Physicochemical Property Comparison of Buprenorphine and Its 3-Alkyl Esters", *Pharm. Res.* (1995), vol. 12, pp. 1526-1529.
Stinchcomb, "Permeation of Buprenorphine and Its 3-Alkyl-Ester Prodrugs Through Human Skin", *Pharm. Res.* (1996), vol. 13, pp. 1519-1523.
International Search Report, Application No. PCT/GB2007/001120, dated Jul. 30, 2007.
Written Opinion of the International Searching Authority, Application No. PCT/GB2007/001120, dated Jul. 30, 2007.

*Primary Examiner* — Charanjit Aulakh
(74) *Attorney, Agent, or Firm* — Fish & Richardson P.C.

(57) ABSTRACT

Ester derivatives of the phenolic hydroxyl group of buprenorphine can be used in the treatment of opiate dependency and/or moderate to severe pain. The esters have an enhanced bioavailability, an enhanced duration of action, and a reduced abuse potential.

39 Claims, 4 Drawing Sheets

Pharmacokinetics of buprenorphine and buprenorphine hemi-adipate after oral administration to dogs

BUPRENORPHINE DERIVATIVES AND USES THEREOF

TECHNICAL FIELD

This invention relates buprenorphine derivatives and uses thereof.

BACKGROUND

The treatment of opiate abuse and dependence by substitution of the abused opiate with a safer, longer-acting opioid is often a successful pharmacotherapeutic intervention strategy. Heroin, a widely abused opiate, acts as an agonist for the muopioid receptor (MOR). Heroin is often abused using intravenous injection, often resulting in needle-sharing among addicts, which is often responsible for the spread of life-threatening infections such as hepatitis C and HIV/AIDS. Methadone has been used as a substitute MOR agonist. Methadone is orally active, and has sufficient duration of action to enable it to be given as a single daily dose. More recently, buprenorphine 1, 21-(cyclopropyl-7α-[(S)-1-hydroxy-1,2,2-trimethylpropyl]-6,14-endo-ethano-6,7,8,14-tetrahydro-oripavine, a MOR partial agonist, has been used as a pharmacotherapy (see, e.g., U.S. Pat. No. 4,935,428). As a partial MOR agonist, it has a lower ceiling to its MOR-mediated effects than a full MOR agonist (e.g., methadone). As a result, buprenorphine has a greater margin of safety than full MOR agonists. In addition, buprenorphine also has a long duration of action. Buprenorphine's enhanced safety, coupled with its extended duration, enables a relatively long dosing interval, typically every 24 hours, but this can be extended to every 72 hours or more.

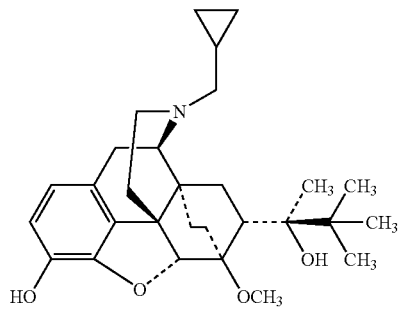

Buprenorphine's favorable safety profile compared to methadone has allowed it to be prescribed by office-based physicians, which has substantially decreased the cost of treatment, and increased the number of addicts in pharmacotherapy treatment.

For the treatment of opiate abuse and dependence, buprenorphine is available as tablets formulated for sublingual administration, and is sold under the trademark Subutex®. The daily maintenance dose for Subutex® is in the range 4-16 mg. Subutex® is readily soluble in aqueous media, making it possible for addicts to misuse the formulation by dissolving the tablets in water, and then injecting the resulting solution. To counter this misuse, buprenorphine has been formulated as a mixture with the MOR antagonist naloxone in a 4:1 ratio (Suboxone®).

Sublingual administration of buprenorphine has several drawbacks, notably the need to avoid swallowing the tablet because of buprenorphine's low bioavailability (~5%) when taken orally. In comparison, buprenorphine's bioavailability is approximately fifty percent when absorbed sublingually (see, e.g., Jasinski and Preston, *Buprenorphine*, Ed. A Cowan, J W Lewis, Wiley-L is, NY pp. 189-211).

Several buprenorphine ester derivatives are described by Stinchcomb et al. in *Pharm. Res* (1995), 12, 1526-1529. The physiochemical properties of the esters are described, and compared with those of buprenorphine hydrochloride and its free base. Stinchcomb et al. also describe transdermal absorption of these esters in *Biol. Pharm. Bull.* (1996), 19, 263-267 and *Pharm. Res*. (1996), 13, 1519-1523. Wang, Published U.S. Patent Application No. 2005/0075361, also describes some buprenorphine derivatives, which are apparently useful for pain relief when delivered intramuscularly or subcutaneously.

SUMMARY

Ester derivatives of the phenolic hydroxyl group of buprenorphine 1 (structure shown above) are described herein. Generally, such derivatives include a moiety that is bonded to the oxygen of the former phenolic hydroxyl group. The moiety can include, e.g., a terminal carboxylic acid group, or an ester of the carboxylic acid group. As described herein, many of such derivatives can be made by reacting buprenorphine with a dicarboxylic acid, the corresponding anhydride or an equivalent thereof, e.g., an ester of the dicarboxylic acid having a good leaving group, e.g., tosylate, iodide, bromide, or chloride. The novel esters, e.g., in solid dosage forms, can be used for treating persons who are physically dependent on opiates, or suffering from pain, e.g., severe or chronic pain. The solid dosage forms can have an excellent safety profile, enhanced duration of action, and a reduced potential for misuse.

In one aspect, the invention features compounds of Structure I, or salts thereof;

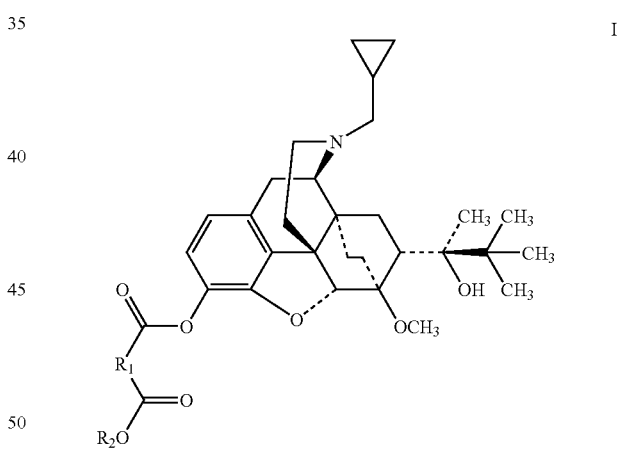

$R_1$ is
  (1) $C_1$-$C_{10}$ straight-chain or branched alkylene, optionally substituted with an aromatic ring,
  (2) —$(CH_2)_p$CH=CH$(CH_2)_p$—, in which each p is independently an integer from 0 to 4,
or
  (3) —$(CH_2)_n$X$(CH_2)_n$—, in which each n is an integer from 0 to 2, X is O, S, NH, N(COOCH$_2$Ph),

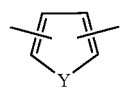

having 1,2-, 1,3-, or 1,4-substitution, in which Y is O, S or NH,

having 1,2-, 1,3-, or 1,4-substitution or

in which m is an integer from 1 to 4;
R$_2$ is H or C$_1$-C$_6$ straight-chain or branched alkyl.

In another aspect, the invention features compounds of Structure IA, or salts thereof;

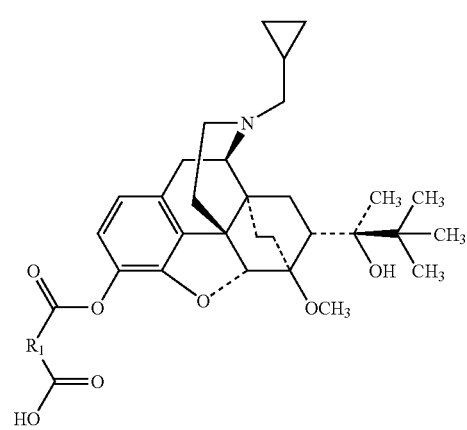

IA

R$_1$ is
(1) C$_1$-C$_{10}$ straight-chain alkylene,
(2) C$_1$-C$_8$ straight-chain alkyl substituted with from 1 to 4 methyl groups or a phenyl group,
or
(3) —(CH$_2$)$_p$CH═CH(CH$_2$)$_p$—, in which each p is independently an integer from 0 to 3.

In another aspect, the invention features the compound of Structure IA1, or salts thereof:

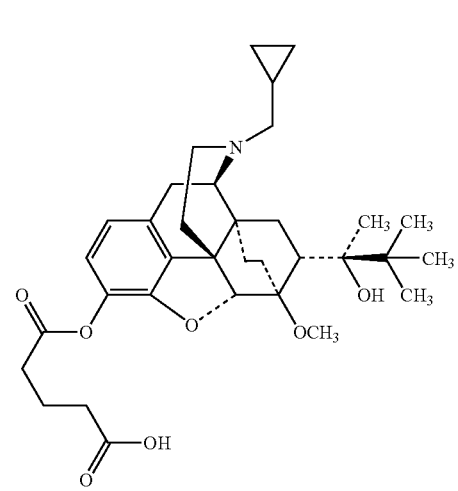

IA1

In another aspect, the invention features the compound of Structure IA2, or salts thereof:

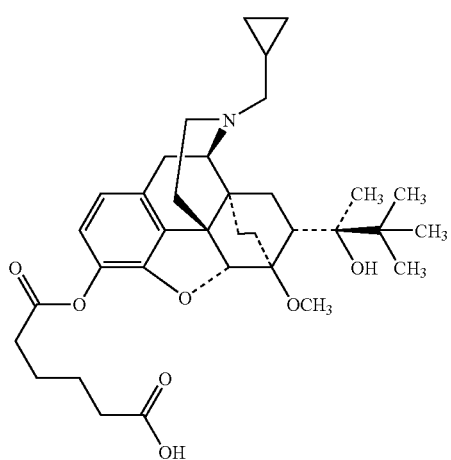

IA2

In yet another aspect, the invention features compounds of Structure II, or salts thereof;

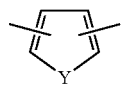

II

Each n is an integer from 0 to 2, X is O, S, NH, N(COOCH$_2$Ph),

having 1,2-, 1,3-, or 1,4-substitution, in which Y is O, S or NH,

having 1,2-, 1,3-, or 1,4-substitution, or

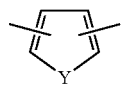

in which m is an integer from 1 to 4.

The compounds and/or compositions described herein include solid dosage forms that can be swallowed, applied sublingually and/or buccally. The compounds and/or compositions described herein can also be administered by other routes, such as intravenously, intramuscularly or transdermally.

In another aspect, the invention features methods of treating opiate abuse and/or dependence in a subject by administering to the subject a therapeutically effective amount of one or more compounds and/or compositions described herein.

In another aspect, the invention features methods of relieving or treating pain in a subject, e.g., a human subject, by administering to the subject a therapeutically effective amount of one or more compounds and/or compositions described herein.

Aspects or embodiments may have any one of the following, or combinations of the following advantages. The compounds and/or compositions described herein are useful in treating opiate dependence. Some of the compounds and/or compositions can have a reduced potential for misuse, at least in part because of their reduced hydrophilicity and reduced solubility in water. Treatments are simple to employ and less prone to be incorrectly performed. The compounds and/or compositions can be employed in treatments outside of a hospital. The compounds and/or compositions are powerful analgesics that can relieve moderate-to-severe pain. The compounds and/or compositions can be administered by a variety of convenient routes, including orally, sublingually, buccally, intravenously, intramuscularly or transdermally. The compounds and/or compositions can be provided in a number of different states, including solids and liquids. The compounds and/or compositions can be provided in a number of convenient forms, including tablets, powders and patches. The compounds and/or compositions can be rendered water-soluble or water-insoluble. The compositions have an enhanced oral bioavailability and an enhanced duration of action. The compounds and/or compositions can have a slower onset of action in comparison to buprenorphine.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, and other references mentioned herein are incorporated by reference herein in their entirety. In case of conflict, the present specification, including definitions, will control.

Other features and advantages of the invention will be apparent from the following detailed description and figures, and from the claims.

DETAILED DESCRIPTION

Figure 1A:
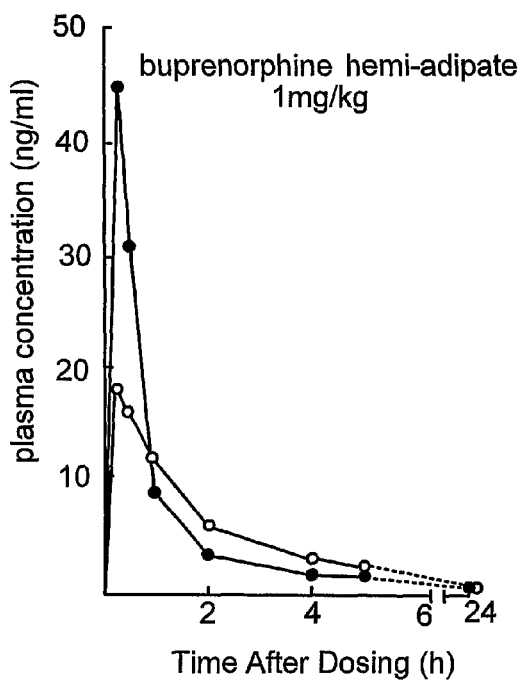
FIG. 1A is a graph showing average plasma concentrations (in ng/ml) of buprenorphine hemiadipate and hydrolysis product buprenorphine as a function of time after oral administration (swallowing) of a dose of 1 mg/kg of buprenorphine hemiadipate to a first group of beagle dogs.

Novel ester derivatives of the phenolic hydroxyl group of buprenorphine are described herein. The novel esters can be used, e.g., to treat persons who are physically dependent on opiates. Various solid dosage forms can be provided that include one or more of the novel esters. The solid dosage forms can be, e.g., swallowed, or applied sublingually.

Buprenorphine Derivatives

The ester derivatives can generally be described as compounds of Structure I or salts of compounds of Structure I.

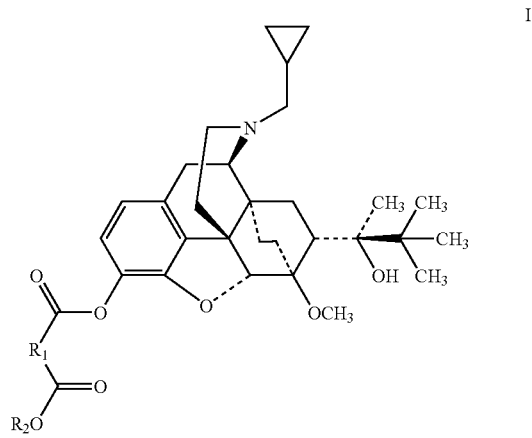

In Structure I, $R_1$ is (1) a $C_1$-$C_{10}$ straight-chain or branched alkylene moiety, optionally substituted with a aromatic ring, e.g., a carbocyclic or heterocyclic aromatic ring; (2) a —$(CH_2)_p$CH=CH$(CH_2)_p$— moiety in which each p is independently an integer from 0 to 4; or (3) a —$(CH_2)_n$X$(CH_2)_n$— moiety in which each n is an integer from 0 to 2, X is O, S, NH, a 5-membered ring represented by Structure 2 (below) having 1,2-(structure 2A below), 1,3-(2B), or 1,4-substitution (2C) in which Y is O, S or NH, a benzene ring represented by Structure 3 (below) having 1,2-(3A), 1,3-(3B), or 1,4-substitution (3C) or a 5-, 6-, 7- or 8-membered alkyl ring, as represented by Structure 4 (below). In instances in which X is a 5-, 6-, 7- or 8-membered alkyl ring, all positional isomers of each respective ring systems can be utilized, e.g., 1,2- and 1,3-substitution for the 5-membered ring. In Structure I, $R_2$ is H or a $C_1$-$C_6$ straight-chain or branched alkyl.

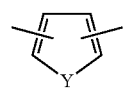
2

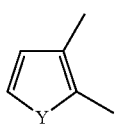
2A

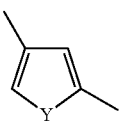
2B

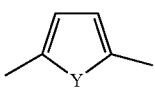
2C

3

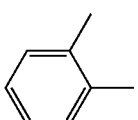
3A

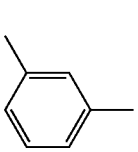
3B

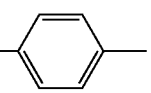
3C

4

Some examples of $C_1$-$C_{10}$ straight-chain or branched alkyl moieties include, e.g., —$CH_2$—, —$CH_2CH_2$—, —$CH_2CH_2CH_2$—, —$CH_2CH_2CH_2CH_2CH_2$— and Structure 5, 6, 7, and 8 below.

5

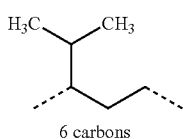
6

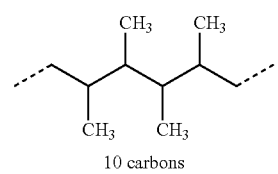

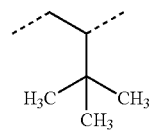
7

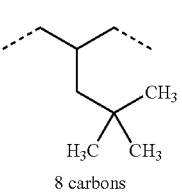
8

Some examples of $C_1$-$C_{10}$ straight-chain or branched alkyl moieties substituted with an aromatic ring include Structure 9, 10, 11, and 12 below.

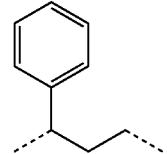
9

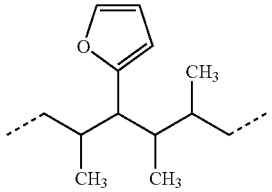
10

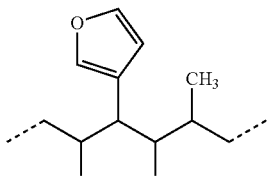
11

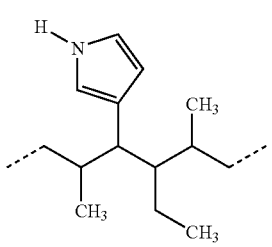
12

The aromatic ring can be, e.g., a single ring or a fused ring. The aromatic ring can be carbocyclic ring (e.g., a benzene ring or a naphthalene ring system), a heterocyclic ring (e.g., a thiophene derivative, a furan derivative, or a pyrrole derivative) or a fused carbocyclic and heterocyclic ring.

In specific embodiments, $R_1$ is —$CH_2CH_2$—, —$CH_2CH_2CH_2$—, —$CH_2CH_2CH_2CH_2$—, —$CH_2CH(CH_3)CH_2$—, —$CH_2C(CH_3)_2CH_2$—, —$CH_2OCH_2$—, —$CH_2SCH_2$—, —$CH_2NHCH_2$—, or —$CH_2N(COOCH_2Ph)CH_2$—.

In instances in which $R_2$ is a $C_1$-$C_6$ straight-chain or branched alkyl moiety, $R_2$ can be, e.g., methyl, ethyl, propyl, isopropyl, butyl, isobutyl, sec-butyl, t-butyl, amyl, isoamyl, 1,2-dimethylpropyl, 1,1-dimethylpropyl, pentyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2,2-trimethylpropyl, and 1,1,2-trimethylpropyl.

In some embodiments, $R_2$ is H, providing compounds of Structure IA, or salts thereof.

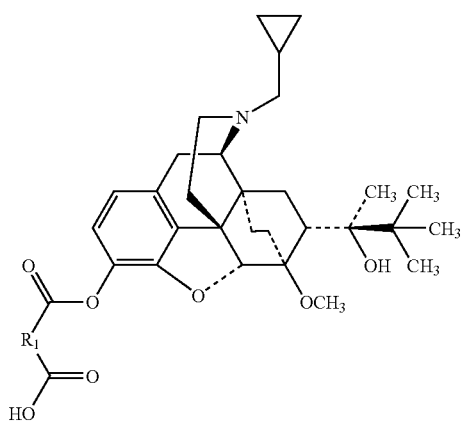

IA

In such instances, in Structure IA, $R_1$ is (1) a $C_1$-$C_{10}$ straight-chain alkylene moiety; (2) a $C_1$-$C_8$ straight-chain alkylene moiety substituted with from 1 to 4 methyl groups or a carbocyclic aromatic ring, e.g., a phenyl group; or (3) a —$(CH_2)_p$CH=CH$(CH_2)_p$— moiety in which each p is independently an integer from 0 to 3.

In some embodiments, compounds or salts of Structure IA are those for which $R_1$ is $C_2$-$C_5$ straight-chain alkylene, e.g., —$CH_2CH_2CH_2$—, —$CH_2CH_2CH_2CH_2$—, —$CH_2CH_2CH_2CH_2CH_2$—, —$CH_2CH(CH_3)CH_2$— or —$CH_2C(CH_3)_2CH_2$—.

In particular embodiments, the compound is that of Structure IA1 or IA2, or a salt of either.

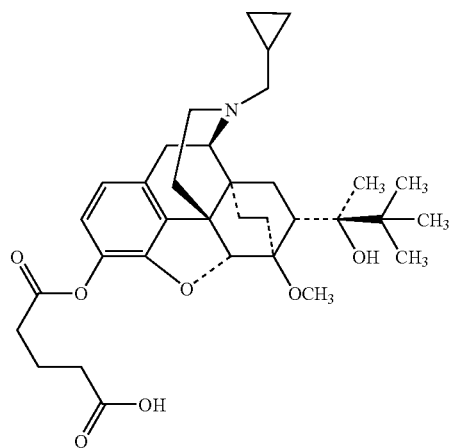

IA1

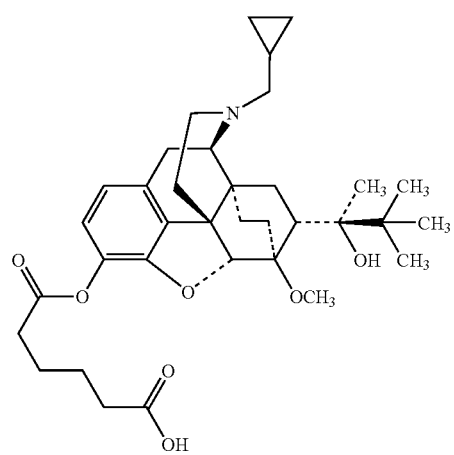

IA2

In some embodiments, $R_2$ is H, and $R_1$ is —$(CH_2)_n$X$(CH_2)_n$—, providing compounds of Structure II, or salts thereof.

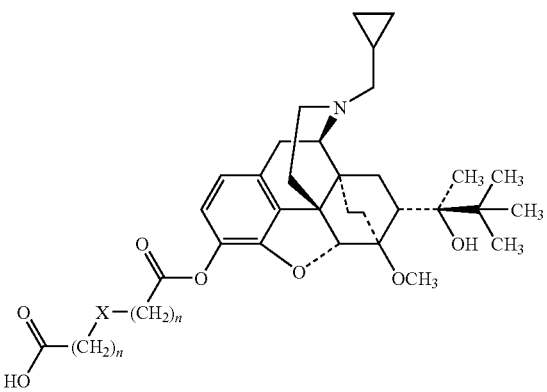

II

In such instances, —$(CH_2)_n$X$(CH_2)_n$— can be any of the moieties described above. In specific embodiments, n is 1 in each occurrence and X is S, NH, N(COOCH$_2$Ph) or O.

Method of Making Buprenorphine Derivatives

Compounds of Structure I can be, e.g., prepared from the acid/free-base (IA) by dissolving the acid/free base in an alcohol, e.g., methanol or ethanol, and then treating the acid/free base solution with the desired diazoalkane ($R_2$—H)N$_2$ 13 of $R_2$. In some embodiments, excess diazoalkane is used. In some embodiments, the diazoalkane is dissolved in an ether, e.g., diethyl ether. In some embodiments, the diazoalkane is added to the acid/free base at a reduced temperature, e.g., less than 50° C., and then after addition, the solution is allowed to warm to room temperature. Esterification of carboxylic acids using diazo compounds is discussed in Furrow, *J. Amer Chem. Soc.*, 126, 12222-12223 (2004). Purification of the ester can be accomplished by passing the crude reaction mixture through a chromatography column containing an adsorbent, e.g., alumina or silica, and then re-crystallizing the obtained material.

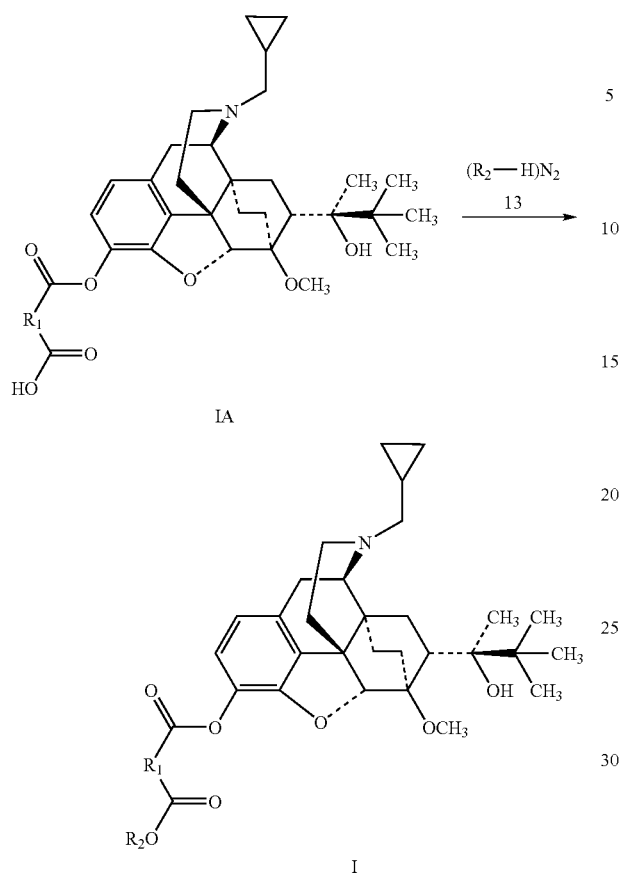

IA

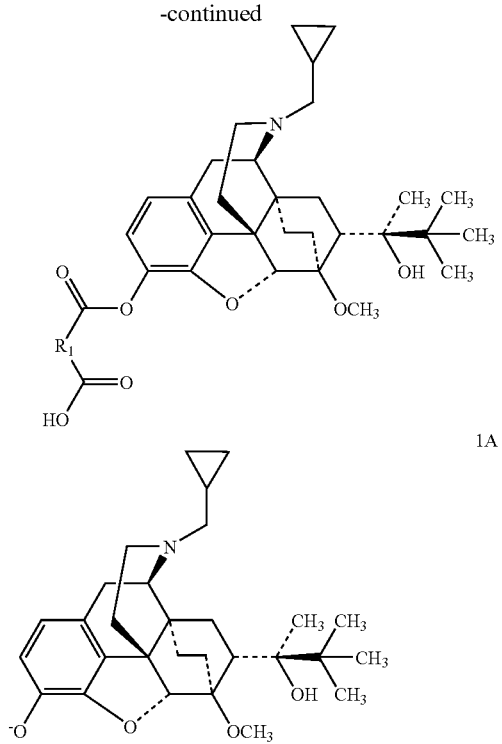

1A

I

Generally, compounds of Structure IA can be, e.g., prepared from buprenorphine 1 or a phenoxy metal salt 1A (e.g., a sodium salt) of buprenorphine with a dicarboxylic acid 14, or an anhydride thereof 15. For example, the dicarboxylic acid can be malonic acid, succinic acid, glutaric acid, 3-methylglutaric acid, 3,3-dimethylglutaric acid, adipic acid, pimelic acid, diglycolic acid, thiodiglycolic acid, imidodiacetic acid, N-benzyloxycarbonyl imidodiacetic acid, terephthalic acid, isophthalic acid, 1,2-naphthalene-dicarboxylic acid, 1H-pyrrole-2,5-dicarboxylic acid, thiophene-2,5-dicarboxylic acid and furan-2,5-dicarboxylic acid.

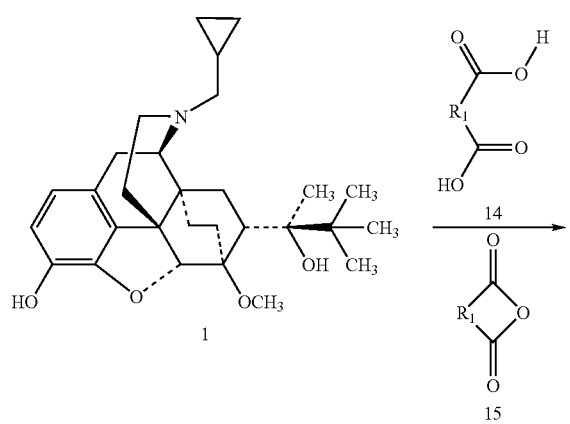

In particular, compounds of Structure I are prepared, e.g., by one of three methods. In a first method, a phenoxy salt 1A, such as the sodium salt of buprenorphine, is prepared and isolated. For example, the sodium salt of buprenorphine can be prepared by reacting buprenorphine, which is dissolved in a solvent such as ethanol/water, with sodium hydride. The phenoxy salt 1A is then reacted with the desired anhydride. The crude salt thus obtained is converted into the hydrochloride salt by treatment with dilute, e.g., 1 M, hydrochloric acid. The acid/free base I can be obtained from the hydrochloride salt by neutralization. In a second method, buprenorphine is reacted in a dry solvent, e.g., a mixture of diethyl ether and acetonitrile, with the desired acid anhydride. Typically after standing overnight at room temperature, the desired hemi-ester is obtained. In a third method, hemi-esters are obtained using the desired dicarboxylic acid by combining the dicarboxylic acid in considerable excess, e.g., greater than a 5-mole excess, with buprenorphine in a dry solvent such as tetrahydrofuran, along with an excess of a coupling agent such as N,N'-dicyclohexylcarbodiimide (DCCI).

Mode of Action of the Buprenorphine Derivatives

Without wishing to be bound by any particular theory, it is believed that the hemi-ester compounds and salts thereof described herein are prodrugs that release active drug buprenorphine in vivo. A prodrug may be defined as a delivery system for a parent drug to which it is metabolically transformed following its absorption, e.g., a biotransformation to liberate the active drug, e.g., hydrolysis. Generally, a prodrug can protect the parent drug from premature inactivation and excretion before reaching its site of action. As examples, heroin (3,6-diacetylmorphine) is a prodrug, though primarily not for morphine, but for 6-acetylmorphine. In this example, the 6-acetoxy group is generally more stable to metabolism than the 3-acetoxy group.

In particular, it is believed that the hemi-esters disclosed are prodrugs that release buprenorphine after hydrolysis in the body of a subject (as shown below).

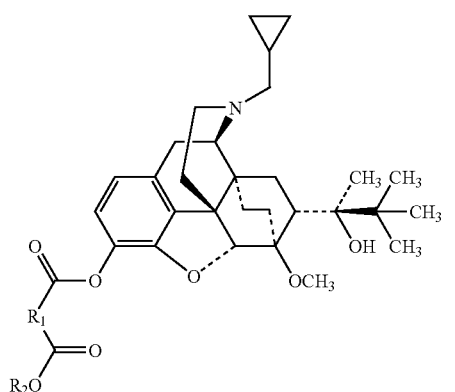

I

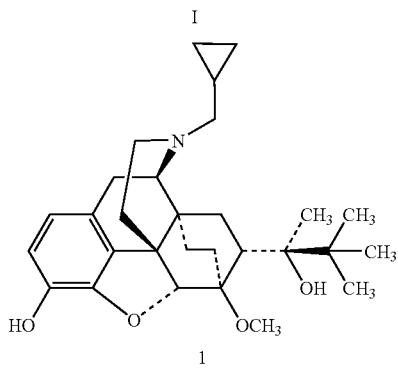

1

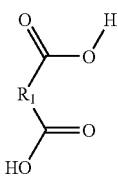

14

The rate of hydrolysis can be controlled by tailoring the hydrophilicity of the hemi-ester. Thus, compounds of Structure I can produce higher blood concentrations of buprenorphine when administered orally (by swallowing) to a subject than are produced by equivalent doses of buprenorphine. This feature can also provide an enhanced duration of action, and a slower onset of action in comparison to buprenorphine.

Referring now to FIGS. 1A, 1B, 2A and 2B, pharmacokinetic studies on beagle dogs were carried out using tritiated hemiadipate 16 and tritiated hemiglutarate 17.

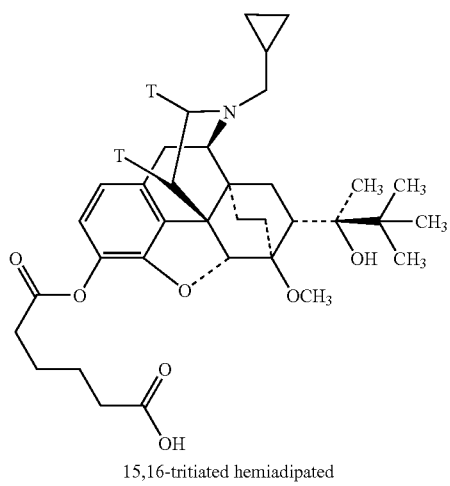

15,16-tritiated hemiadipated

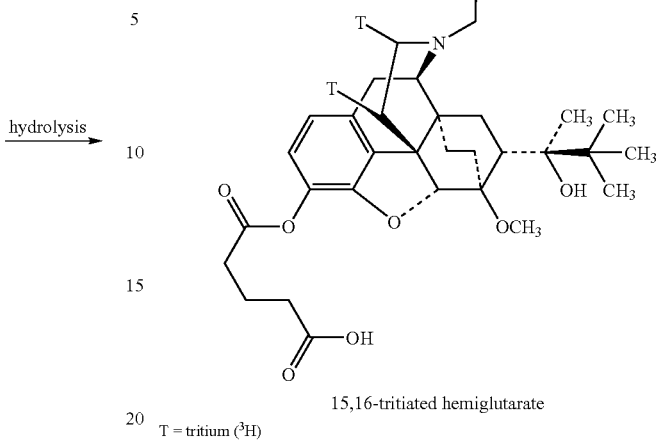

15,16-tritiated hemiglutarate

T = tritium ($^3$H)

Figure 1B:
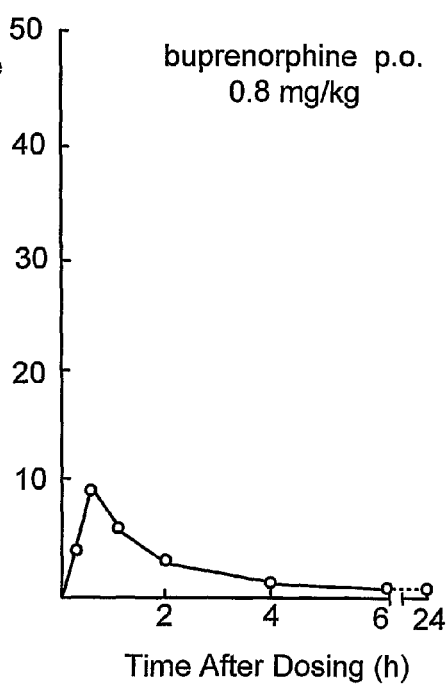
FIG. 1B is a graph showing average plasma concentrations (in ng/ml) of buprenorphine as a function of time after oral administration (swallowing) of a dose of 0.8 mg/kg of buprenorphine to a second group of beagle dogs.
Figures 2A, 2B:
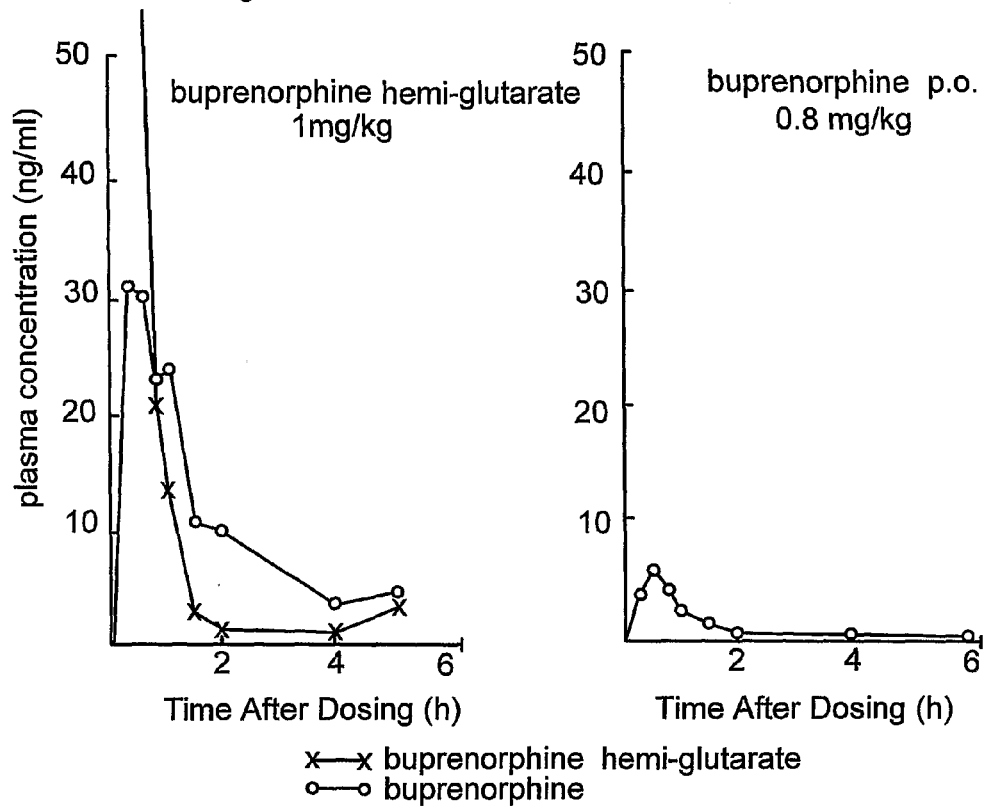
FIG. 2A is a graph showing average plasma concentrations (in ng/ml) of buprenorphine hemiglutarate and hydrolysis product buprenorphine as a function of time after oral administration (swallowing) of a dose of 1 mg/kg of buprenorphine hemiglutarate to the first group of beagle dogs.
FIG. 2B is a graph showing average plasma concentrations (in ng/ml) of buprenorphine as a function of time after oral administration (swallowing) of a dose of 0.8 mg/kg of buprenorphine to the second group of beagle dogs.

FIG. 1A is a graph showing average plasma concentrations (in ng/ml) of buprenorphine hemiadipate and hydrolysis product buprenorphine as a function of time after oral administration (swallowing) of a dose of 1 mg/kg of buprenorphine hemiadipate to a first group of beagle dogs. For comparison, FIG. 1B is a graph showing average plasma concentrations (in ng/ml) of buprenorphine as a function of time after oral administration (swallowing) of a dose of 0.8 mg/kg of buprenorphine to a second group of beagle dogs. FIG. 2B is a graph showing average plasma concentrations (in ng/ml) of buprenorphine hemiglutarate and hydrolysis product buprenorphine as a function of time after oral administration (swallowing) of a dose of 1 mg/kg of buprenorphine hemiglutarate to the first group of beagle dogs. For comparison, FIG. 2B is a graph showing average plasma concentrations (in ng/ml) of buprenorphine as a function of time after oral administration (swallowing) of a dose of 0.8 mg/kg of buprenorphine to the second group of beagle dogs. These studies showed that at times up to 1 hour after administration of 1 mg/kg of the buprenorphine hemi-ester (either hemiadipate or hemiglutarate), high concentrations of intact ester were present in plasma. These levels were higher than those of the liberated buprenorphine, but rapidly fell to become lower than the levels of buprenorphine by 2 hours. In each study (FIGS. 1B and 2B) another group of animals received an equivalent dose of unesterified buprenorphine. The plasma level of buprenorphine following oral administration of doses nearly equivalent to the doses of the hemi-esters in the beagle dogs were significantly lower than those resulting from administration of the hemi-esters. Thus, the hemi-esters each afforded 2 to 3 fold higher blood levels of buprenorphine than was obtained from the parent drug.

Pharmaceutical Compositions

Generally, pharmaceutical compositions are those that include at least one buprenorphine hemi-ester as described herein, and/or at least one salt thereof, as an active ingredient. The pharmaceutical compositions typically include a pharmaceutically acceptable carrier. As used herein the language "pharmaceutically acceptable carrier" includes material such as saline, solvents, dispersion media, coatings, tablet excipients, antibacterial and antifungal agents, isotonic and absorption delaying agents, which are compatible with pharmaceutical administration. Supplementary active compounds can also be incorporated into the compositions. Examples of a supplementary active compound are naloxone, naltrexone and nalmefene.

Pharmaceutical compositions are typically formulated to be compatible with their intended route of administration. Examples of routes of administration include parenteral, e.g., intravenous, intradermal, or subcutaneous; oral; transdermal (topical); and transmucosal (e.g., sublingually, by inhalation and rectal) administration.

Methods of formulating suitable pharmaceutical compositions are described in, e.g., the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates and agents for the adjustment of tonicity, such as sodium chloride or dextrose. pH can be adjusted with acids or bases, such as hydrochloric acid or sodium hydroxide. Parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms, such as bacteria and fungi. The carrier can be a solvent or dispersion medium containing, e.g., water, ethanol, polyol (e.g., glycerol, propylene glycol, and liquid polyethylene glycol), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal agents, e.g., parabens, chlorobutanol, phenol, ascorbic acid and thimerosal. In many cases, it will be preferable to include isotonic agents, e.g., sugars, polyalcohols such as mannitol, sorbitol, and/or sodium chloride in the composition. Prolonged absorption of the injectable compositions can be brought about by including in the composition an agent that delays absorption, e.g., aluminum monostearate and gelatin.

Sterile injectable solutions can be prepared by incorporating the active compound in the desired amount in an appropriate solvent with one or a combination of ingredients enumerated above, as desired, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In some embodiments, the compositions described herein are specially adapted for oral administration. For the purpose of oral therapeutic administration, the one or more hemi-ester active compound (or salt thereof) can be incorporated with excipients and used in the form of tablets, troches, or capsules, e.g., gelatin capsules; such compositions will generally include an inert diluent or an edible carrier. Oral compositions can also be prepared using a fluid carrier for use as a mouthwash. Pharmaceutically compatible binding agents and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Systemic administration of a therapeutic compound as described herein can also be by transmucosal or transdermal means. For transmucosal or transdermal administration, penetrants appropriate to the barrier to be permeated are used in the formulation. Such penetrants include, e.g., for transmucosal administration, detergents, bile salts, and fusidic acid derivatives. Transmucosal administration can be accomplished through the use of nasal sprays or suppositories. For transdermal administration, the one or more hemi-ester active compounds (and/or salts thereof) are formulated into ointments, salves, gels, or creams.

For administration by inhalation, the one or more hemi-ester active compounds (and/or salts thereof) are formulated in the form of an aerosol spray from a pressured container or dispenser that contains a suitable propellant, e.g., a gas such as carbon dioxide, or a nebulizer. Carrier materials customarily used in dry powder formulations can also be used, e.g., mono- or disaccharides, such as glucose, lactose, lactose monohydrate, sucrose or trehalose, sugar alcohols, such as mannitol or xylitol, polylactic acid or cyclodextrin, glucose, trehalose and in particular lactose monohydrate. In some embodiments, the formulations can also contain two or more carrier materials. If desired, in addition to noninhalable carrier particles, the formulation can also contain a proportion of inhalable carrier particles; for example in addition to relatively coarse lactose monohydrate carrier particles it can contain a proportion of, e.g., 0.1 to 10% by weight of micronized lactose monohydrate, which can have, e.g., a particle size diameter of at most 10 μm, preferably at most 5 μm, for at least 50% of the particles. Dry powder formulations including the compounds described herein can be used in a dry powder inhaler as is known in the art, e.g., multidose dry powder inhalers that contain a powder reservoir, e.g., as described in WO97/20589. A number of other methods and devices suitable for delivery of compounds by inhalation are described, e.g., in U.S. Pat. No. 6,645,466.

The pharmaceutical compositions can also be prepared in the form of suppositories (e.g., with conventional suppository bases such as cocoa butter and other glycerides) or retention enemas for rectal delivery.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially, e.g., from Alza Corporation and Nova Pharmaceuticals, Inc.

Methods of Treatment

The methods described herein include methods for the treatment of opiate abuse and dependence. In some embodiments, the opiate abused is heroin. Generally, the methods include administering a therapeutically effective amount of a buprenorphine hemi-ester as described herein, to a subject who is in need of, or who has been determined to be in need of, such treatment. As used in this context, to "treat" opiate abuse and dependence means to reduce or eliminate the subject's dependence on the abused drug, to remove the addicting drug from the addicted subject's body, and, to some degree, to hinder the subject from reestablishing a dependence on that drug. Treat also means to prevent or minimize the subject experiencing withdrawal symptoms or cravings for drugs of abuse, e.g., by employing a maintenance dosing regime.

Also described herein are methods for the treatment of pain, e.g., severe or chronic pain. Generally, the methods include administering a therapeutically effective amount of a buprenorphine hemi-ester as described herein, to a subject who is in need of, or who has been determined to be in need of, such treatment, e.g., a subject suffering from pain, e.g., severe or chronic pain. As used in this context, to "treat" pain means to ameliorate, reduce, or eliminate the subject's perception of pain.

Dosage, toxicity and therapeutic efficacy of the compounds can be determined, e.g., by standard pharmaceutical procedures in cell cultures and/or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

The data obtained from animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in a method described herein, the therapeutically effective dose can be estimated initially from cell culture assays. A dose can be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, e.g., by high performance liquid chromatography with appropriate detection systems and the data used to determine appropriate doses and inter-dose periods to maintain buprenorphine at levels that prevent withdrawal effects and that are consistent with clinically acceptable levels delivered by sublingual buprenorphine tablets.

An "effective amount" is an amount sufficient to effect beneficial or desired results. For example, a therapeutic amount is one that achieves the desired therapeutic effect. An effective amount can be administered in one or more administrations, applications or dosages. For example, the compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments. Generally, the compositions will be administered daily to establish the patient in treatment with the potential to increase the inter-dose period once the patient is stabilized. However by way of guidance it may be stated that in a human being treated for drug dependency dosages of about 2-30 mg of a compound of Structure I are required to give a potentially beneficial effect. A supplementary active compound such as, naltrexone or nalmefene may be present to deter misuse of the composition. The weight ratio of a compound of Structure I to a supplementary active compound present to deter misuse of the composition, such as naloxone, naltrexone or nalmefene, is suitably in the range 2:1 to 8:1, preferably 2.5:1 to 6:1, preferably 3:1 to 5:1, preferably 3.5:1 to 4.5:1.

The following examples are illustrative and are not intended to be limiting.

EXAMPLES

Example A

Synthesis of Buprenorphine Hemisuccinate

Sodium Phenoxide Method

Buprenorphine (2.35 g, 0.005 mol) was added to a warm solution of sodium hydride (50% dispersion in oil; 0.24 g, 0.005 mol NaH) in 2:1 ethanol:$H_2O$ (9 ml). After stirring for 30 minutes, the solvent was removed by repeated azeotroping with benzene. The residue was finally dried over phosphorus pentoxide in vacuo. This crude sodium salt was dissolved in dry benzene (30 ml), and then succinic anhydride (0.5 g, 0.005 mol) was added and the mixture was stirred for 1.5 hours. After removal of benzene, the residue was shaken with 2N hydrochloric acid (50 ml) for 2 hours. The hydrochloride salt so obtained was filtered, washed with water and dried. Recrystallization from isopropanol followed by washing of the filtered product with hot methanol gave pure salt (1.0 g), mp 214-216° C. (decomp.). Found (percent) C, 64.95; H, 7.6; N, 2.2; Cl, 6.25. $C_{33}H_{43}NO_7$(HCl)(½$H_2O$) requires C, 64.84; H, 7.4; N, 2.3; Cl, 5.8; 3480 (OH), 1757 and 1735 in $cm^{-1}$.

Anhydride Method

Buprenorphine (1.7 g, 0.0036 mol) and succinic anhydride (1.1 g, 0.011 mol) were dissolved in a warm 3:5 mixture of dry ether:acetonitrile (40 ml). After standing overnight, the desired hemisuccinate (1.65 g) was filtered and dried, mp 195-197° C. (decomp.). A further quantity of material (0.1 g) was obtained from the mother liquors when they were allowed to stand for an addition further 24 hours. Found (percent) C, 69.9; H, 7.8; N, 2.4. $C_{33}H_{49}NO_7$ requires C, 70.0; H, 7.65; N, 2.5; 3460 (OH), 1760 and 1733 in $cm^{-1}$.

Example B

Synthesis of Buprenorphine Hemiglutarate

A solution of buprenorphine (2.1 g, 0.0045 mol) and glutaric anhydride (1.6 g, 0.014 mol) in dry 3:5 ether:acetonitrile (50 ml) was stirred at room temperature for 5 days, during which time buprenorphine hemiglutarate glutaric acid salt precipitated as a dense white solid. The solid was filtered off and washed with dry ether (40 ml). This washing gave the salt as a white crystalline solid (1.4 g), melting point 160-161.5° C. The salt was dissolved in a minimum amount of cold methanol (12 ml), and then excess dry ether (60 ml) was added followed by ethereal HCl. This resulted in the precipitation of a white solid that was filtered off and washed with dry ether. Recrystallization from methanol/ether gave pure buprenorphine hemiglutarate as the hydrochloride monohydrate (0.9 g), melting point 214-215° C. (decomp.). Found (percent) C, 63.85; H, 7.75; N, 2.08. $C_{34}H_{47}NO_7(HCl)(H_2O)$ requires C, 64.18; H, 7.92; N, 2.20; 3340 (OH), 1750 and 1720 in $cm^{-1}$.

Example C

Synthesis of Buprenorphine Hemiadipate

Buprenorphine (96 g, 0.2 mol) was dissolved in freshly dried tetrahydrofuran. To this was added adipic acid (129.2 g, 0.8 mol) and DCCI (100 g, 0.48 mol). The mixture was stirred for 6 days, and then further quantities of adipic acid (30 g) and DECI (25 g) were added. This reaction mixture was stirred for three days. After such time, stirring was stopped and the mixture was allowed to settle for three days. The solids were filtered off and then the solvent was removed from the soluble material. Dissolution in a minimum quantity of methanol, followed by the addition of ethanol/HCl afforded the solid hydrochloride of buprenorphine hemiadipate (86 g), which was purified by recrystallization from ethanol. The purified material had melting point of 270-272° C. (decomp.). Found (percent) C, 66.49; H, 8.12; N, 2.23; Cl, 5.53. $C_{35}H_{50}NO_7Cl$ requires C, 66.49; H, 7.97; N, 2.22; Cl, 5.61; 3440 (OH) 1762 and 1739 in $cm^{-1}$.

Alternate Method: To a stirred solution of 4-dimethylaminopyridine (1.232 g, 0.010 mol, acylation catalyst) in tetrahydrofuran (1.5 L, THF) was added buprenorphine free base (93.534 g, 0.20 mol) followed by adipic acid (239.952 g, 1.64 mol). The suspension was stirred for 20 minutes and dicyclohexylcarbondiimide (45.409 g, 0.22 mol) was added over approx 30 minutes whilst maintaining the internal temperature between 16-21° C. with cold water cooling. Stirring was continued overnight. The insoluble precipitate (mostly dicyclohexylurea) was removed by filtration under vacuum and washed with more THF. Solvent was removed under vacuum from the filtrate (960 ml recovered). The precipitate (mainly adipic acid) was removed by filtration and washed with a little more THF and dried in air. The combined filtrates were stirred at room temperature and treated with concentrated hydrochloric acid (20.606 g, 0.20 mol). The resulting precipitate was removed by filtration, washed with THF and dried in air. This crude product was crystallized from ethanol/dichloromethane with a hot filtration and removal of solvents under vacuum to concentrate the suspension. The solid was removed by filtration, washed with ethanol and dried to give buprenorphine hemiadipate hydrochloride (87.525 g). The identity of the material was confirmed by full assignment of the $^1H$ and $^{13}C$ NMR spectrum and by comparison of these spectra with the NMR spectra of buprenorphine hydrochloride.

Example D

Synthesis of Buprenorphine Hemi-3-methylglutarate

A solution of buprenorphine (6.8 g, 0.0146 mol) and 3-methylglutaric anhydride (5.13 g, 0.04 mol) was stirred in a 3:5 mixture of dry ether:acetonitrile (160 ml) for two days at room temperature, after which time TLC ($SiO_2$, methanol/ethylacetate/880 ammonia, 25:74.5:0.5) showed a significant quantity of buprenorphine remaining. A further quantity of anhydride was added, and stirring was continued for and additional 24 hours. The reaction mixture was poured into dry ether (600 ml), and then ethereal HCl was added. The resultant precipitant was filtered and crystallized from methanol/ether. This gave buprenorphine methylglutarate hydrochloride hydrate as a white crystalline solid (4.5 g). The solid was recrystallized three more times to give 1.8 g, melting point 213-216° C. (decomp.). Found (percent) C, 63.73; H, 8.16; N, 2.10; $C_{35}H_{47}NO_6(HCl)(H_2O)$ requires C, 64.65; H, 8.06; N, 2.15.

Example E

Synthesis of Buprenorphine Hemi-3,3-dimethylglutarate

To a solution of buprenorphine (7.05 g, 0.015 mol) in a 1:3 mixture of dry ether/benzene (200 ml) was added sodium hydride (0.72 g, 0.015 mol, 50% dispersion in oil). After stirring at room temperature for 0.5 hours, 3,3-dimethylglutaric anhydride (4.26 g, 0.03 mole) was added. Stirring was continued for 7 hours, after which time a further quantity of sodium hydride (0.72 g, 0.015 mol) and 3,3-dimethylglutaric anhydride (4.0 g, 0.028 mole) was added. After two days at room temperature the mixture was evaporated to dryness and methanol (20 ml) was added. The solution was eluted down a silica column using ethyl acetate/0.5% 880 ammonia. The first three fractions contained pure buprenorphine; the remaining fractions consisted of the desired hemi-ester. The fractions were combined, dissolved in a minimum amount of methanol (10 ml) and excess ether was added followed by ethereal HCl. The solid which precipitated was filtered off and recrystallized five times from ethanol/ether to give buprenorphine hemi-3,3-dimethylglutarate so hydrochloride as a white crystalline solid (1.5 g) melting point 216-219° C. (decomp.). Found (percent) C, 66.39; H, 8.50; N, 2.16; $C_{36}H_{51}NO_7(HCl)$ required C, 66.91; H, 8.11; N, 2.17; 3300 (OH), 1730 and 1720 in $cm^{-1}$.

Example F

Synthesis of Buprenorphine Hemidiglycolate

A solution of buprenorphine (6.8 g, 0.0146 mol) and diglycolic anhydride (5.1 g, 0.044 mol) in a 3:5 mixture of dry ether:acetonitrile (100 ml) was stirred overnight at room temperature. Ethereal HCl was added followed by dry ether (500 ml), producing a dense white precipitate, which was filtered off, washed with dry ether and dried. Two re-crystallizations from ethanol/ether gave buprenorphine hemidiglycolate as the hydrochloride monohydrate (4.5 g), melting point 186-189° C. (decomp.). Found (percent) C, 62.04; H, 7.73; N, 2.10; $C_{33}H_{45}NO_8(HCl)(H_2O)$ requires C, 62.10; H, 7.78, N, 2.19; 1780, 1760 and 1720 in $cm^{-1}$.

Example G

Synthesis of Buprenorphine Hemithiodiglycolate

Thiodiglycolic anhydride was prepared according to the method of Morril et al., *J. Org. Chem.*, 26, 4103 (1961). Thiodiglycolic acid (32.4 g, 0.216 mol) and phosphorous trichloride (9.2 g, 5.5 ml, 0.065 mol) were stirred at 55° C. in chloroform (40 ml) until no HCl gas evolution ceased. The mixture was then heated at reflux for 1 hour, after which an additional amount (4.6 g, 2.9 ml, 0.033 mol) of phosphorous trichloride was added. After the addition, an oil precipitated and refluxing was continued for an additional 1 hour. The hot chloroform solution was then decanted away from the oil and set aside to cool. A white crystalline solid was deposited, which was filtered and dried (24.6 g). A TLC (SiO$_2$, chloroform/methanol 4:1) showed one major component, plus a very small amount of the starting di-acid. A solution of buprenorphine (6.8 g, 0.0146 mol) and thiodiglycolic anhydride (11.6 g, 0.088 mol) in a 3:5 mixture of dry ether:acetonitrile (160 ml) was stirred at room temperature for 6 hours. An oil precipitated and stirring was stopped. The mixture was allowed to stand for 48 hours. A white solid formed, which was filtered off and dissolved in hot methanol (25 ml). Dry ether (500 ml) was added followed by ethereal HCl. A white solid precipitated (6.4 g). A 2.5 g portion of this was re-crystallized from methanol/ether to give the desired buprenorphine hemi-dithioglycolate hydrochloride monohydrate (2.1 g), melting point 225-226° C. (decomp.). Found (percent) C, 60.50; H, 7.30; N, 2.03: $C_{33}H_{45}NO_7S(HCl)(H_2O)$ requires C, 60.57; H, 7.39; N, 2.14; 3300 (OH), 1745, and 1710 in cm$^{-1}$.

Example H Synthesis Buprenorphine Hemiiminodiacetate

N-Benzyloxycarbonyliminodiacetic acid dicyclohexylamine salt was taken up in a mixture of 10% citric acid and ethyl acetate and shaken vigorously. Solid citric acid was added until the two layers had become clear; the ethyl acetate layer was separated off, washed with water and brine, dried using MgSO$_4$ and evaporated to give a yellow oil. A portion of this was reacted at 0° C. with an equimolar quantity of N,N'-dicyclohexyl-carbodiimine in methylene chloride for 1 hour, and then at room temperature for 2 hours. Dicyclohexylurea was filtered off and the methylene chloride was evaporated to give the anhydride as a white solid. Recrystallization from ethyl acetate/petroleum ether gave N-benzyloxycarbonyliminodiacetic anhydride as a white crystalline solid. 1800, 1770, 1680 in cm$^{-1}$.

A solution of N-benzyloxycarbonyliminodiacetic anhydride (5.9 g, 0.025 mol) and buprenorphine (4.3 g, 0.009 mol) in a 3:5 mixture of dry ether:acetonitrile (102 ml) was stirred at room temperature for 24 hours. Buprenorphine hemi-N-benzyloxycarbonyl-iminodiacetate precipitated and was filtered off and then washed with ether (7.2 g), melting point 133-137° C.; Found (percent) C, 66.64; H, 7.44; N, 4.29; $C_{41}H_{52}N_2O_9(H_2O)$ requires C, 67.00; H, 7.41; N, 3.81). 3400 (OH), 1770 and 1700 in cm$^{-1}$.

Buprenorphine hemi-N-benzyloxycarbonyliminodiacetate (2.0 g, 0.0028 mol) was dissolved in dry tetrahydrofuran (100 ml) and 10% Pd on charcoal was added (0.25 g). The suspension was stirred at room temperature and hydrogen gas was bubbled through. After 4 hours, TLC showed that very little starting material remained. The Pd/C was filtered off and dry ether (600 ml) was added to the filtrate. Ethereal HCl was added and, after scratching a side of the flask, a white solid was precipitated. This was filtered off and dried in-vacuo over phosphorous pentoxide. The solid (1.2 g) was relatively insoluble in ethanol, but was very soluble in methanol. After washing with ethanol, the product was dissolved in methanol (a small quantity of insoluble solid was filtered off) and ether was added. This gave a white crystalline solid, which was filtered off (0.25 g). TLC (SiO$_2$, CM20) showed one major product plus a small buprenorphine contaminant. Two more re-crystallizations from methanol/ether gave a purified buprenorphine hemiiminodiacetate dihydrochloride monohydrate (0.1 g), melting point 214° C.; Found (percent) C, 58.96; H, 7.59; N, 3.17, $C_{33}H_{46}N_2O_7(2HCl)(H_2O)$ requires C, 58.83; H, 7.48; N, 4.16). 3450 (OH), 1770 and 1630 in cm$^{-1}$.

Example I

Synthesis of 3-(3-carbomethyloxypropionyl) Buprenorphine

Buprenorphine hemisuccinate (2.1 g) (see Example A) was stirred in methanol (50 ml) and treated with excess ethereal diazomethane (freshly distilled). After removal of methanol, the residue was dissolved in ethyl acetate and filtered through a column of alumina (grade I; 9"×1"). The filtrate was evaporated and the residue was crystallized from ether/light petroleum ether, giving 1.58 g of material having a melting point of 119.5-121° C.; Found (percent) C, 70.3; H, 7.8; N, 2.5. $C_{33}H_{45}NO_7$ requires C, 70.45; H, 7.8; N, 2.4. 3440 (OH), 1766, and 1750 in cm$^{-1}$.

The hydrochloride salt was prepared with HCl/ether, melting point 254-254.5° C. Found (percent) C, 66.0; H, 7.8; N, 2.4; Cl, 5.9. $C_{34}H_{45}NO_7(HCl)$ requires C, 66.3; H, 7.5; N, 2.3; Cl, 5.57). 3450 (OH), 1763, 1735 and 1618 in cm$^{-1}$.

Example J

In-Vitro Pharmacokinetics

In-vitro hydrolysis of hemi-esters of buprenorphine was measured in plasma or blood of various species (for results, see TABLE 1 below).
a. Radiochemicals: Radiolabelled hemi-esters of buprenorphine were prepared from [15,16-$^3$H] buprenorphine 18 using the esterification methods described above, e.g., by reaction of 18 with the appropriate anhydride to give the desired hemi-ester. Specific activities varied in the range of 20-800 μCi/mg.

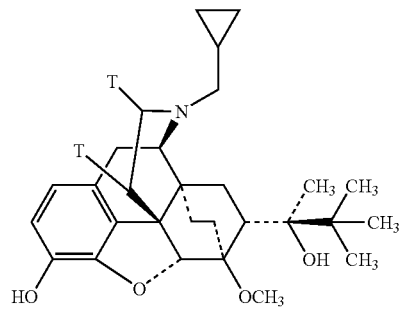

Structure of [15,16-$^3$H] buprenorphine 18; T=tritium
b. Blood and Plasma: Blood was obtained from human volunteers, beagle dogs or baboons by vena puncture and from other species by terminal cardiac puncture. Blood was collected into heparinized plastic tubes and plasma, if required, obtained by centrifugation (3,000 g, 10 minutes). Plasma, if not used immediately, was stored at −20° C.
c. In-vitro Incubations: Studies were carried out at 37° C. by means of a thermostatically controlled shaking water bath. Samples of plasma or blood (with or without added buffer) were allowed to warm to 37° C. in conical glass tubes before incubations were initiated by the addition of a suitable aliquot (3-30 μl) of an aqueous solution of the hemi-ester hydrochloride. Incubations were performed at an initial concentration of 0.1-30 μg/ml.

At various times during incubation, aliquots of plasma or blood (100 μl) were removed into Eppendorf plastic tubes, quick-frozen in a cardice/acetone bath and methanol (100 μl) added. Tubes were vortexed then centrifuged in an Eppendorf 3200 centrifuge (1 minute) and the supernatant chromatographed as described below.

d. Thin Layer Chromatography: TLC was conducted on Merck silica gel 60 $F_{254}$ plates (0.25 mm thickness). The following solvent systems were used:
  i. Chloroform/methanol 20:1 (v/v) containing 0.5% v/v $NH_4OH$ (specific gravity 0.88).
  ii. Ethyl acetate/methanol 75:25 (v/v) containing 1% v/v $NH_4OH$ (specific gravity 0.88)

Methanolic supernatants described earlier were applied to the origin of 20×5 cm plates, dried and eluted in the appropriate system. Authentic marker samples of ester and buprenorphine were co-chromatographed to be visualized later under short wave U.V. light. After elution the silica was removed as 1 cm zones into scintillation vials and shaken with 2 ml water and 5 ml of ES299 (Packard) or similar based scintillant. Vials were counted for $^3H$ (as cpm) in a Packard 2450 or Intertechnique SL 4221 scintillation spectrometer.

e. Treatment of Results: Radiochromatogram results were expressed as intact ester remaining as a percentage of the total radioactivity recovered. The results were presented graphically on semi-logarithmic paper against time and first-order half-life values obtained from the straight lines obtained.

f. Results: The results are shown in TABLE 1.

TABLE 1

First order in-vitro half-life values for buprenorphine hemiadipate in the plasma and buffered blood of various species

| Species | Initial ester concentration (μg/ml) | t½ plasma (hours) | t½ buffered blood (hours) |
| --- | --- | --- | --- |
| Human | 3.0 | 4.3-4.8 | 7.5-9.6 |
|  | 0.25 | 3.3-4.8 | — |
| Dog | 3 | 24 | 4.6 |
| Baboon | 3 | 5 | — |
| Rat | 3 | 0.4 | 0.18 |
| Guinea Pig | 3 | 0.16 | 0.10 |
| Rabbit | 3 | 0.07 | 0.03 |
| Mouse | 3 | 0.03 | 0.02 |

These results demonstrate that the buprenorphine hemi-adipate survives in plasma and releases buprenorphine over an extended period of time.

Example K

In-Vivo Pharmacokinetics

Determinations of plasma levels of buprenorphine and buprenorphine hemi-esters were made in beagle dogs following oral administration of buprenorphine hemi-adipate and buprenorphine hemi-glutarate, using a gas chromatographic/mass spectrometry method of analysis (gc/ms).

a. In-vivo Administration: Beagle dogs were chosen to model the pharmacokinetic parameters of esterase activity, which is responsible for the in-vivo hydrolysis of the hemi-esters to buprenorphine. The choice was made following an extensive in-vitro study of several esters in the whole blood and plasma of several animal species in comparison with human blood and plasma. It was found that blood from rodent species—rat, mouse, guinea pig and rabbit, with high esterase activity, rapidly hydrolyzed the hemi-esters whereas higher species—dog and baboon, behaved like human blood in effecting much slower hydrolysis (see TABLE 1). Thus, the dog was chosen as the preferred experimental animal.

For the adipate hemi-ester, the pharmacokinetic investigation was repeated at a much higher dose (63 mg/kg) administered orally to beagle dogs in comparison to an equivalent dose (50 mg/kg) of the parent buprenorphine.

b. Blood sampling and storage: Blood samples (2 ml) were taken by venepuncture at 0.5, 1, 2, 5, 8 and 24 hours after administration of the dose. In order to minimize any possible hydrolysis of the hemi-esters, the blood samples were stored on ice immediately after collection, the plasma separated in a refrigerated centrifuge, transferred to plain tubes, and stored at −20° C. until assayed.

c. Analytical methods

For Free Buprenorphine

All extraction and derivatization operations were carried out in glassware silanized by treatment with 5% trimethylchlorosilane (TMCS) in toluene.

Plasma (0.25 ml) in a 15 ml conical centrifuge tube was mixed with 10 μl (1 μg) of the internal standard, N-n-propyl-norbuprenorphine in methanol. Re-distilled AR diethyl ether (5 ml) was added, the tube vortex mixed for 1 minute and centrifuged at 2000 rpm for 10 minutes. The ether layer was transferred to a clean tube and the process repeated with 4 ml of ether. The combined ether layers were evaporated to dryness under a $N_2$ stream and the tubes containing the extracted residues placed in a desiccator over phosphorous pentoxide for 16-24 h to remove traces of water. To the dried residues were added toluene (redistilled AR) (20 μl), triethylamine in toluene (0.1 M, 20 μl) and heptafluorobutyric anhydride (HFBA, 10 μl). After thorough mixing for 1 minute, the solution was allowed to stand for 15 minutes at room temperature. Phosphate buffer (0.5 M, pH 6.0, 50 μl) was added to hydrolyze any unreacted HFBA and the tube mixed for 30 seconds. After centrifuging at 2000 rpm for 10 minutes, a portion (5 μl) of the upper organic phase was taken for gc/ms.

For Total Buprenorphine

Plasma (0.25 ml) in a 15 ml conical centrifuge tube was mixed with 10 μl (1 μg) of internal standard solution and glycine-sodium hydroxide buffer (ether-washed, 0.2 M, pH 10.4, 0.25 ml). After mixing for 30 seconds the tube was stoppered and allowed to stand at room temperature for 18 hours in order to hydrolyze any unchanged buprenorphine adipate.

After hydrolysis, the plasma sample was transferred to a Clin-Elut™ tube (type CE 1003, Scientific Marketing Associates, London), and allowed to adsorb onto the bed. Three portions of redistilled diethyl ether (3×5 ml) were poured through the tube, and collected in a clean conical centrifuge tube. The ether was evaporated under a stream of $N_2$ gas and the tube transferred to a desiccator over phosphorous pentoxide.

Toluene (20 μl) and heptafluorobutyrylimidazole (HFBI, 20 μl) were added to the dried residue, mixed for 1 minute and allowed to stand at room temperature for 15 minutes. The reaction mixture was evaporated to dryness at room temperature under nitrogen and the residue treated with toluene (30 μl). A portion of this extract was taken for gc/ms.

Calibration Curve

A calibration curve prepared from stock solutions was run each day'prior to the analysis during the day of all of the samples from three dogs receiving the same dose. For the 0.4 and 4.0 mg/kg doses, the calibration range was from 2-20 ng/0.25 ml of plasma, and for the 40 mg/kg dose 5-50 ng/0.25 ml. Similar calibration lines were carried through the hydrolysis procedure. Plots of peak height ratio versus amount of buprenorphine added were constructed for each day's analysis, and used to quantify results from samples processed during that day.

d. Instrumentation

Combined gas-chromatography/mass spectroscopy (gc/ms) was performed using a Pye 104 gas chromatograph coupled via a stainless steel two-stage jet separator to an LKB 2091 mass spectrometer. The glass column (1 m×4 mm i.d.) was packed with 3% OV-1 on Gas-Chrom Q™ (100-120 mesh) JJ's Chromatography, Kings Lynn) conditioned overnight at 300° C. The flow rate of the helium carrier gas was 30 ml/minute. Operating temperatures for the gas chromatograph column, the separator and the ion source were 290° C., 280° C., and 290° C., respectively. An ionizing voltage of 20 eV and trap current of 50 µA were used.

Selected ion monitoring of m/e 562 (base peak of internal standard HFB derivative) was performed by rapid switching of the accelerating voltage using the LKB 2091-710 M.I.D. accessory. The 3.5 KV voltage calibration constant for m/e 562 was 52620. Other M.I.D. operating parameters were as follows: pre-amplifier gain setting 3, multiplier voltage setting 800, peak duration 64 seconds and M.I.D. gain over the range 10 to 500. The signals from the monitored channels were recorded on an SE 3006 UV oscillographic recorder with a chart speed of 1 cm/minute. Peak height ratios of the ions were calculated and reference made to the daily calibration line for quantitation.

e. Results

Figures 3A, 3B:
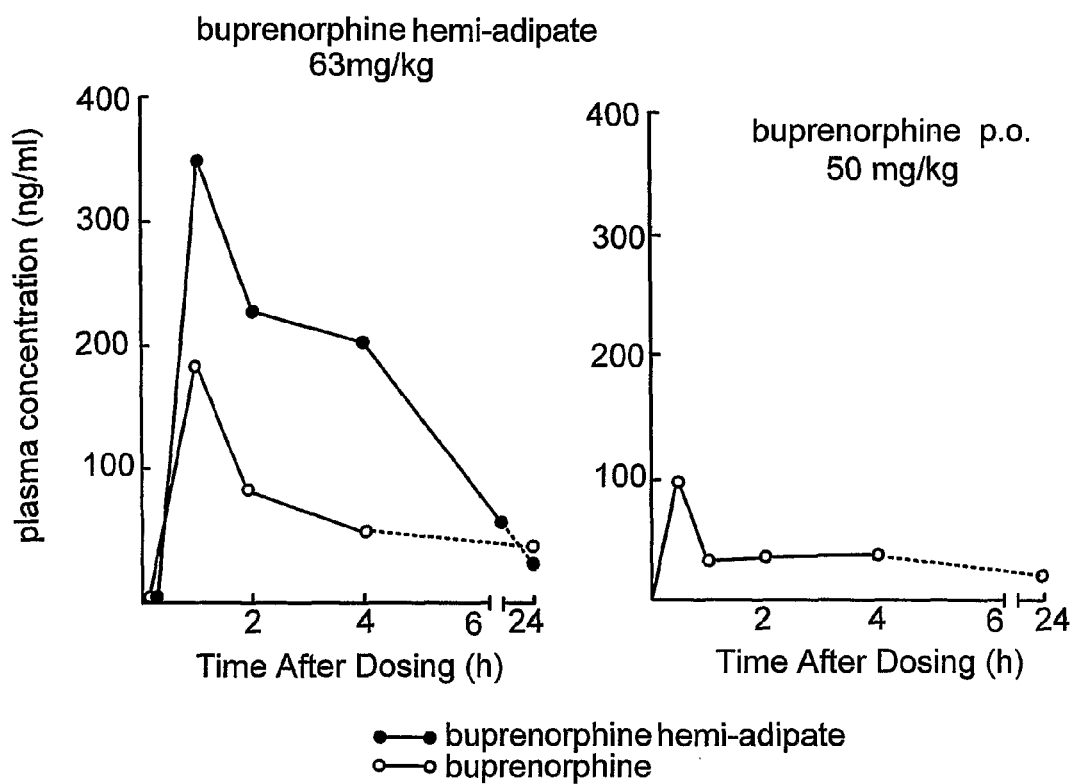
FIG. 3A is a graph showing average plasma concentrations (in ng/ml) of buprenorphine hemiadipate and hydrolysis product buprenorphine as a function of time after oral administration (swallowing) of a dose of 63 mg/kg of buprenorphine hemiadipate to a first group of beagle dogs.
FIG. 3B is a graph showing average plasma concentrations (in ng/ml) of buprenorphine as a function of time after oral administration (swallowing) of a dose of 50 mg/kg of buprenorphine to a second group of beagle dogs.

FIG. 3A is a graph showing average plasma concentrations (in ng/ml) of buprenorphine hemiadipate and hydrolysis product buprenorphine as a function of time after oral administration (swallowing) of a dose of 63 mg/kg of buprenorphine hemiadipate to a first group of beagle dogs; and FIG. 3B is a graph showing average plasma concentrations (in ng/ml) of buprenorphine as a function of time after oral administration (swallowing) of a dose of 50 mg/kg of buprenorphine to a second group of beagle dogs. This is a repeat of the of the results described above (see FIGS. 1A and 1B), only using a much higher dose (63 mg/kg, FIG. 3A) administered orally to beagle dogs in comparison to an nearly equivalent dose (50 mg/kg, FIG. 3B) of the parent buprenorphine. As was the case at the lower dose, the plasma levels of the intact ester (unhydrolyzed ester) were substantially higher than those of the liberated buprenorphine and the intact ester plasma concentrations were maintained for 6 hours. The peak level of buprenorphine from the ester was achieved after 1 hour and was about twice the peak level achieved from the unesterified buprenorphine.

Figure 4:
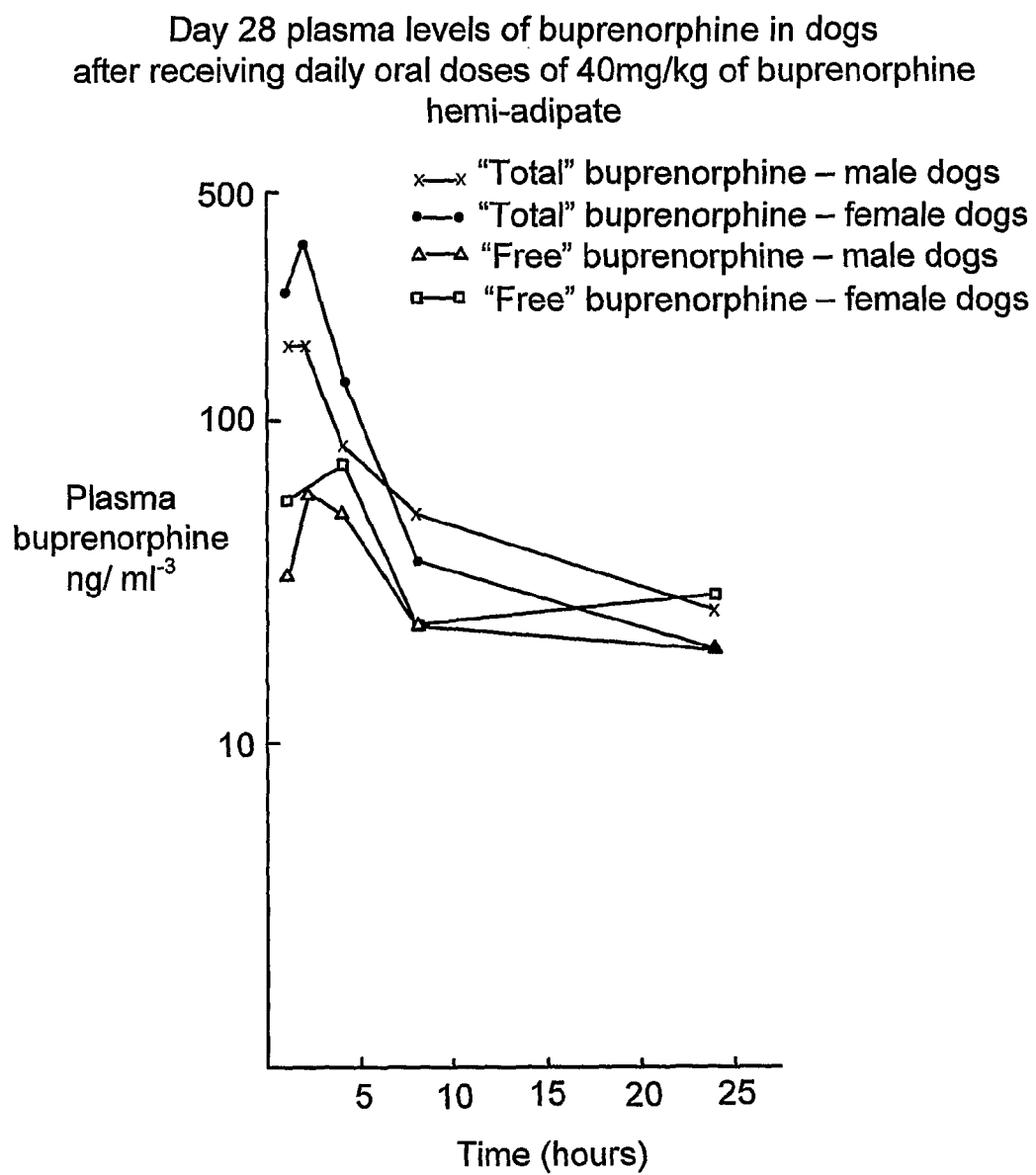
FIG. 4 is a graph showing a pharmacokinetic profile of a high oral dose of buprenorphine hemiadipate administered daily for 28 days to beagle dogs.

The pharmacokinetic profile from a high oral dose of buprenorphine hemi-adipate administered daily for 28 days to beagle dogs is shown in FIG. 4. On day 28, the plasma levels of buprenorphine liberated from the ester were maintained for over 24 hours, whereas the levels of intact ester declined rapidly after 2 hours. Male dogs and female dogs showed these profiles though there were not qualitatively equivalent.

These pharmacokinetic profiles show that the buprenorphine hemi-adipate has a higher oral bioavailability than can be obtained from buprenorphine alone. At the high doses that are used in the treatment of opiate abuse, it is expected that the duration of action of the hemi-esters (or salts thereof) described herein will be longer than can be achieved by an equivalent dose of buprenorphine, as reflected in the sustained plasma levels of the hemi-adipate described above. Additionally, it is expected that peak plasma levels of the hemi-esters (or salts thereof) described herein will be achieved significantly later than those achieved by an equivalent dose of buprenorphine.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. Compounds of Structure I, or salts thereof:

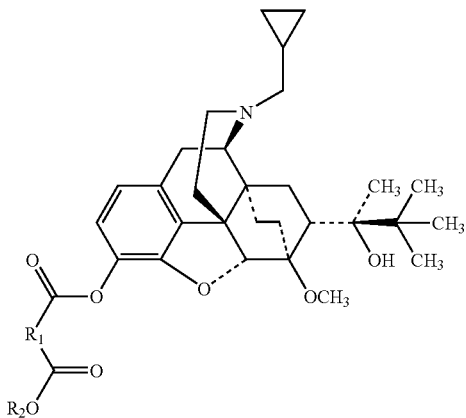

wherein $R_1$ is
(1) $C_1$-$C_{10}$ straight-chain or branched alkylene, optionally substituted with an aromatic ring,
(2) —$(CH_2)_p CH$=$CH(CH_2)_p$—, in which each p is independently an integer from 0 to 4,
or
(3) —$(CH_2)$—$X(CH_2)_n$—, in which each n is an integer from 0 to 2, X is O, S, NH, N(COOCH$_2$Ph),

having 1,2-, 1,3-, or 1,4-substitution, in which Y is O, S or NH,

having 1,2-, 1,3-, or 1,4-substitution or

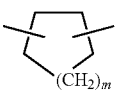

in which m is an integer from 1 to 4;
and wherein $R_2$ is H or $C_1$-$C_6$ straight-chain or branched alkyl.

2. Compounds of claim 1, wherein $R_1$ is selected from the group consisting of
—CH₂CH₂—, —CH₂CH₂CH₂—, —CH₂CH₂CH₂CH₂—, —CH₂CH(CH₃)CH₂—, —CH₂C(CH₃)₂CH₂—, —CH₂OCH₂—, —CH₂SCH₂—, —CH₂NHCH₂— and —CH₂N(COOCH₂Ph)CH₂—.

3. Compounds of claim 2, wherein $R_2$ is H.

4. Compounds of Structure IA, or salts thereof:

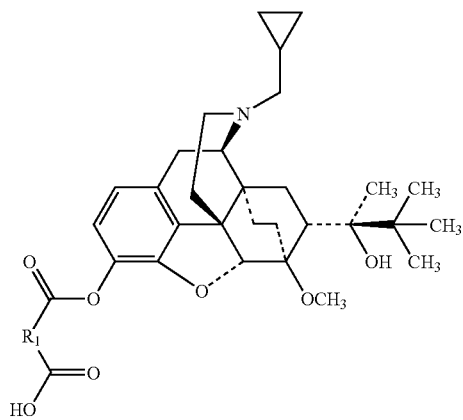

IA wherein $R_1$ is
(1) $C_1$-$C_{10}$ straight-chain alkylene,
(2) $C_1$-$C_8$ straight-chain alkylene substituted with from 1 to 4 methyl groups or a phenyl group,
or
(3) —(CH₂)$_p$CH=CH(CH₂)$_p$—, in which each p is independently an integer from 0 to 3.

5. Compounds of claim 4, wherein $R_1$ is $C_2$-$C_5$ straight-chain alkylene.

6. Compounds of claim 5, wherein $R_1$ is selected from the group consisting of —CH₂CH₂CH₂—, —CH₂CH₂CH₂CH₂— and —CH₂CH₂CH₂CH₂CH₂—.

7. The compound of claim 6, wherein $R_1$ is —CH₂CH₂CH₂—.

8. The compound of claim 6, wherein $R_1$ is —CH₂CH₂CH₂CH₂—.

9. Compounds of claim 4, wherein $R_1$ is —CH₂CH(CH₃)CH₂— or —CH₂C(CH₃)₂CH₂—.

10. Compounds of Structure II, or salts thereof:

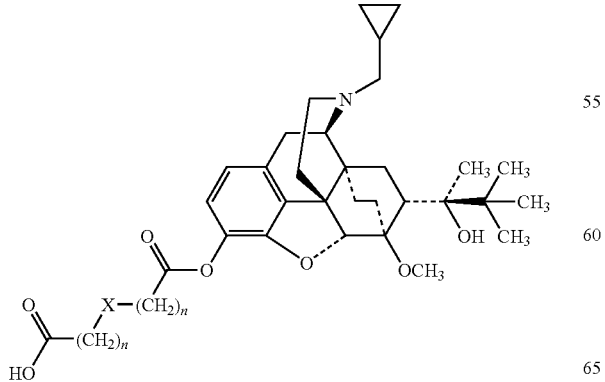

II wherein each n is an integer from 0 to 2, and X is O, S, NH, N(COOCH₂Ph),

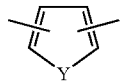

having 1,2-, 1,3-, or 1,4-substitution, in which Y is O, S or NH,

having 1,2-, 1,3-, or 1,4-substitution or

in which m is an integer from 1 to 4.

11. Compounds of claim 10, wherein each n is 1.

12. Compounds of claim 11, wherein X is S, NH or N(COOCH₂Ph).

13. The compound of claim 11, wherein X is O.

14. The compound of Structure IA1:

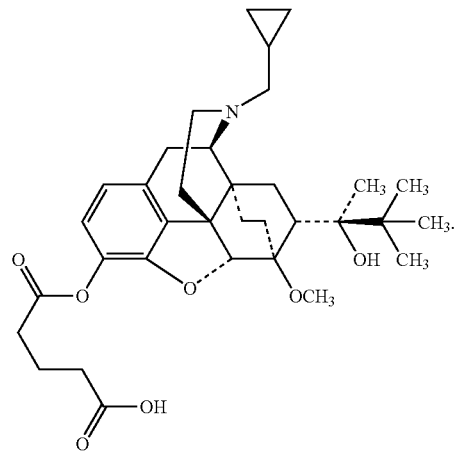

IA1

15. The compound of Structure IA2:

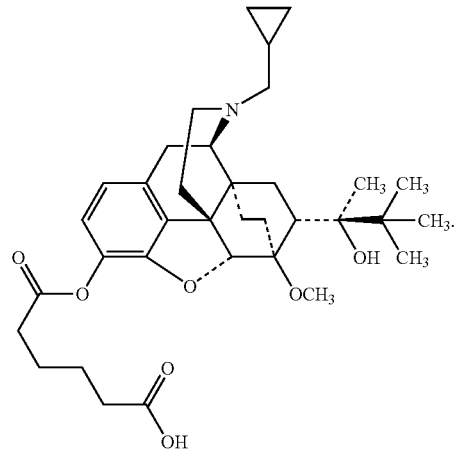

IA2

16. A pharmaceutical composition comprising
(A) a compound of Structure I, or a salt thereof:

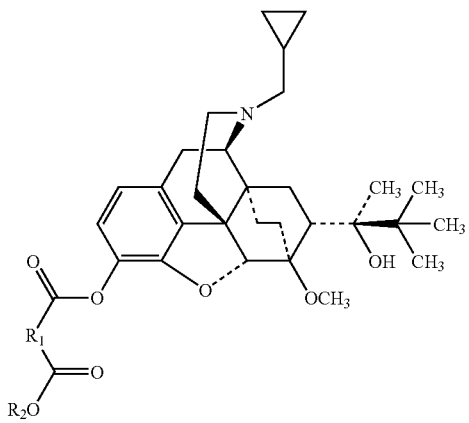

I wherein $R_1$ is
(1) $C_1$-$C_{10}$ straight-chain or branched alkylene, optionally substituted with an aromatic ring,
(2) —$(CH_2)_p$CH=CH$(CH_2)_p$—, in which each p is independently an integer from 0 to 4,
or
(3) —$(CH_2)$—X$(CH_2)_n$—, in which each n is an integer from 0 to 2, X is O, S, NH, N(COOCH$_2$Ph),

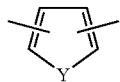

having 1,2-, 1,3-, or 1,4-substitution, in which Y is O, S or NH,

having 1,2-, 1,3-, or 1,4-substitution or

in which m is an integer from 1 to 4;
and wherein $R_2$ is H or $C_1$-$C_6$ straight-chain or branched alkyl, and
(B) a pharmaceutically acceptable carrier.

17. A pharmaceutical composition according to claim 16 in which the compound has Structure IA or a salt thereof:

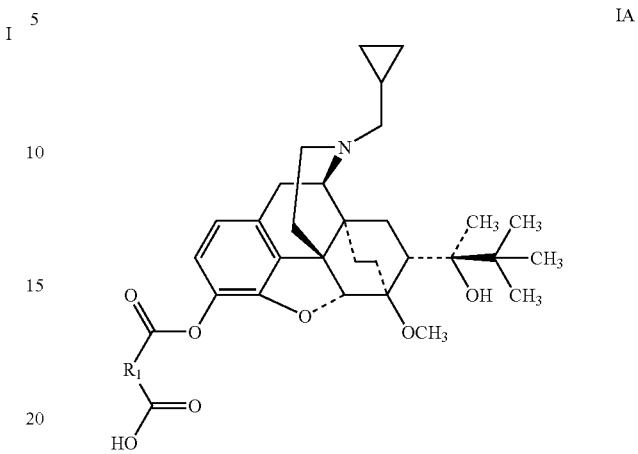

IA wherein $R_1$ is
(1) $C_1$-$C_{10}$ straight-chain alkylene,
(2) $C_1$-$C_8$ straight-chain alkylene substituted with from 1 to 4 methyl groups or a phenyl group,
or
(3) —$(CH_2)_p$CH=CH$(CH_2)_p$—, in which each p is independently an integer from 0 to 3.

18. A pharmaceutical composition according to claim 16 in which the compound has Structure II or a salt thereof:

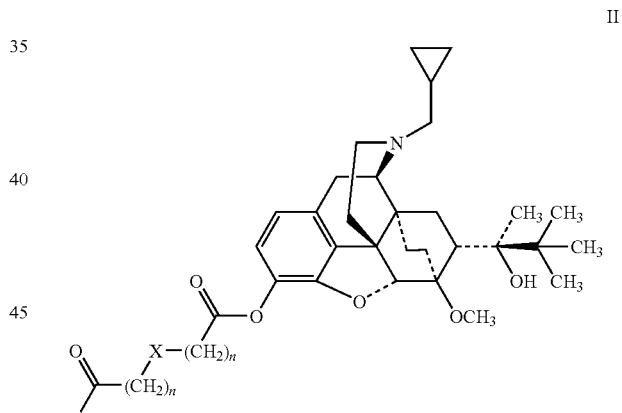

II wherein each n is an integer from 0 to 2, and X is O, S, NH, N(COOCH$_2$Ph),

having 1,2-, 1,3-, or 1,4-substitution, in which Y is O, S or NH,

having 1,2-, 1,3-, or 1,4-substitution, or

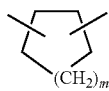

in which m is an integer from 1 to 4.

19. A composition according to claim 17 in which the compound has Structure IA1:

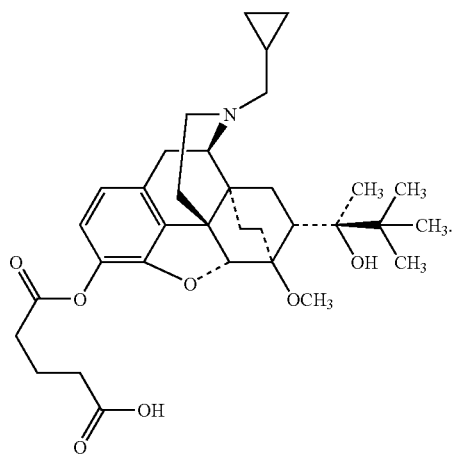

IA1

20. A composition according to claim 17 in which the compound has the structure IA2:

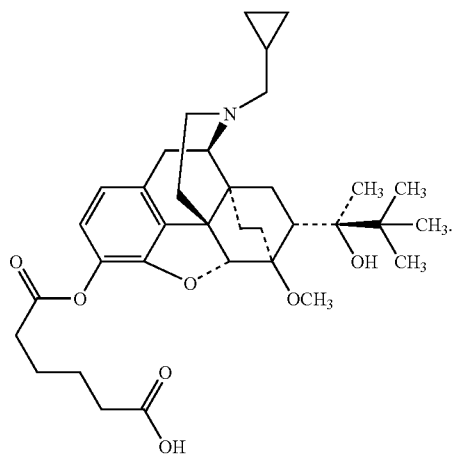

IA2

21. A method of treating opiate abuse and/or dependence in a subject, the method comprising administering to the subject a therapeutically effective amount of one or more compounds of the Structure I, or salts thereof:

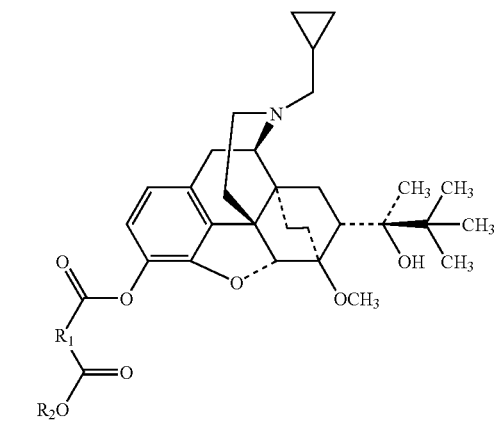

I wherein $R_1$ is
- (1) $C_1$-$C_{10}$ straight-chain or branched alkylene, optionally substituted with an aromatic ring,
- (2) —$(CH_2)_p$CH=CH$(CH_2)_p$—, in which each p is independently an integer from 0 to 4, or
- (3) —$(CH_2)$—X$(CH_2)_n$—, in which each n is an integer from 0 to 2, X is O, S, NH, N(COOCH$_2$Ph),

having 1,2-, 1,3-, or 1,4-substitution, in which Y is O, S or NH,

having 1,2-, 1,3-, or 1,4-substitution or

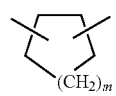

in which m is an integer from 1 to 4;
and wherein $R_2$ is H or $C_1$-$C_6$ straight-chain or branched alkyl.

22. A method according to claim 21, in which is the compounds, $R_1$ is selected from the group consisting of —CH$_2$CH$_2$—, —CH$_2$CH$_2$CH$_2$—, —CH$_2$CH$_2$CH$_2$CH$_2$—, —CH$_2$CH(CH$_3$)CH$_2$—, —CH$_2$C(CH$_3$)$_2$CH$_2$—, —CH$_2$OCH$_2$—, —CH$_2$SCH$_2$—, —CH$_2$NHCH$_2$— and —CH$_2$N(COOCH$_2$Ph)CH$_2$—.

23. A method according to claim 22 in which, in the compounds, $R_2$ is H.

24. A method according to claim 21 in which the compounds have the structure IA, or salts thereof:

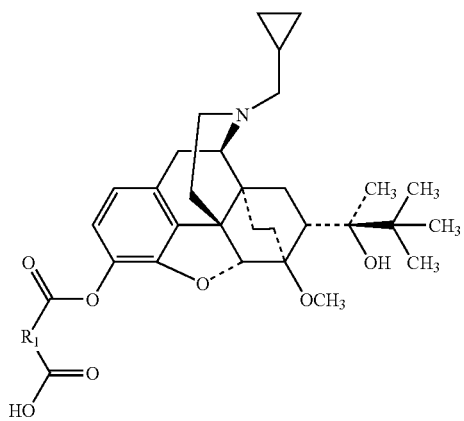

wherein $R_1$ is
  (1) $C_1$-$C_{10}$ straight-chain alkylene,
  (2) $C_1$-$C_8$ straight-chain alkylene substituted with from 1 to 4 methyl groups or a phenyl group,
  or
  (3) —$(CH_2)_p$CH=CH$(CH_2)_p$—, in which each p is independently an integer from 0 to 3.

25. A method according to claim 24 in which, in the compounds, $R_1$ is $C_2$-$C_5$ straight-chain alkylene.

26. A method according to claim 25 in which, in the compounds, $R_1$ is selected from the group consisting of —$CH_2CH_2CH_2$—, —$CH_2CH_2CH_2CH_2$— and —$CH_2CH_2CH_2CH_2CH_2$—.

27. A method according to claim 26 in which, in the compounds, $R_1$ is —$CH_2CH_2CH_2$—, or —$CH_2CH_2CH_2CH_2$—.

28. A method according to claim 21 in which the compounds have the Structure II or salts thereof:

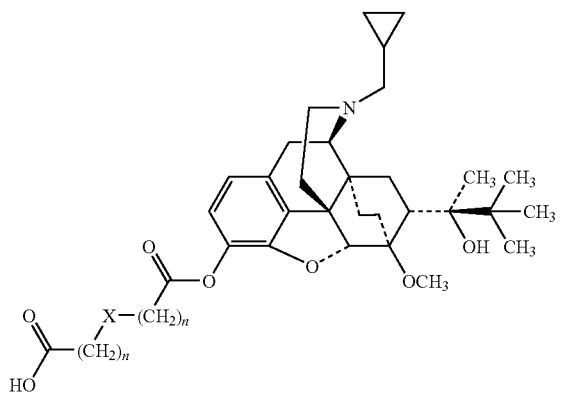

wherein each n is an integer from 0 to 2, and X is O, S, NH, N(COOCH$_2$Ph),

having 1,2-, 1,3-, or 1,4-substitution, in which Y is O, S or NH,

having 1,2-, 1,3-, or 1,4-substitution, or

in which m is an integer from 1 to 4.

29. A method according to claim 28 in which, in the compounds, each n is 1.

30. A method according to claim 29 in which, in the compounds, X is S, NH or N(COOCH$_2$Ph).

31. A method according to claim 29 in which, in the compound, X is O.

32. A method according to claim 24 in which the compound has the Structure IA1:

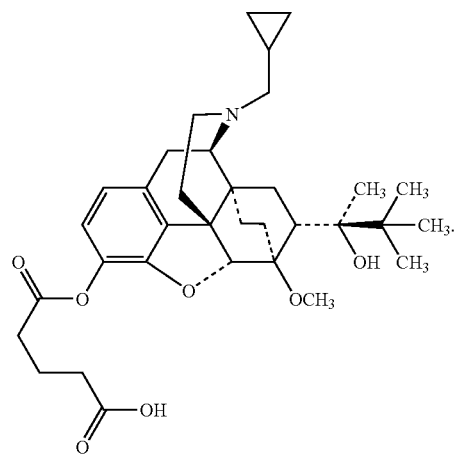

33. A method according to claim 24 in which the compound has the structure IA2:

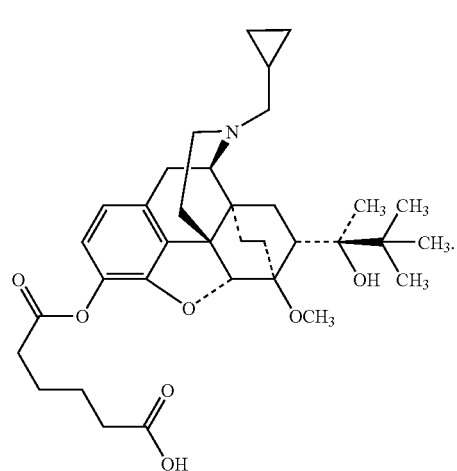

34. A method according to claim 21 in which the one or more compounds is administered orally or sublingually.

35. A method of relieving or treating moderate to severe pain in a subject, the method comprising administering to the subject a therapeutically effective amount of one or more compounds of the Structure I, or salts thereof:

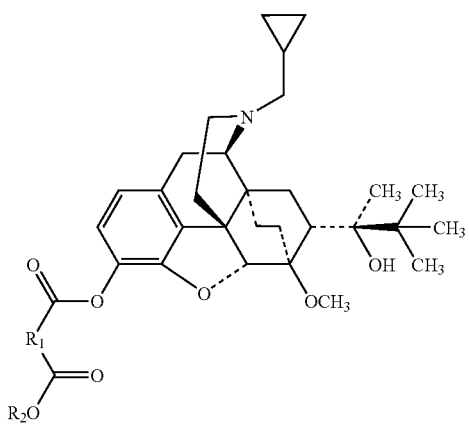

I wherein $R_1$ is
- (1) $C_1$-$C_{10}$ straight-chain or branched alkylene, optionally substituted with an aromatic ring,
- (2) —$(CH_2)_p CH=CH(CH_2)_p$—, in which each p is independently an integer from 0 to 4, or
- (3) —$(CH_2)$—$X(CH_2)_n$—, in which each n is an integer from 0 to 2, X is O, S, NH, N(COOCH$_2$Ph),

having 1,2-, 1,3-, or 1,4-substitution, in which Y is O, S or NH,

having 1,2-, 1,3-, or 1,4-substitution or

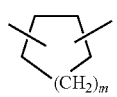

in which m is an integer from 1 to 4;
and wherein $R_2$ is H or $C_1$-$C_6$ straight-chain or branched alkyl.

36. A method according to claim 35 in which the compounds have the structure IA, or salts thereof:

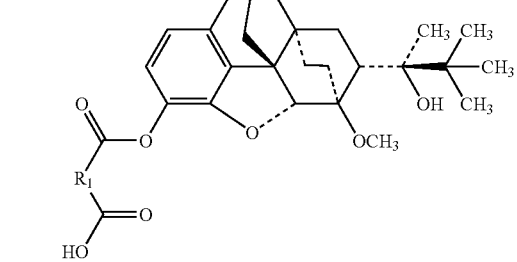

IA wherein $R_1$ is
- (1) $C_1$-$C_{10}$ straight-chain alkylene,
- (2) $C_1$-$C_8$ straight-chain alkylene substituted with from 1 to 4 methyl groups or a phenyl group, or
- (3) —$(CH_2)_p CH=CH(CH_2)_p$—, in which each p is independently an integer from 0 to 3.

37. A method according to claim 35 in which the compounds have the Structure II or salts thereof:

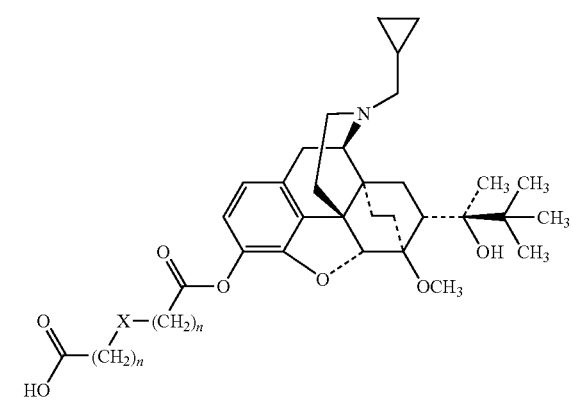

II wherein each n is an integer from 0 to 2, and X is O, S, NH, N(COOCH$_2$Ph),

having 1,2-, 1,3-, or 1,4-substitution, in which Y is O, S or NH,

having 1,2-, 1,3-, or 1,4-substitution, or

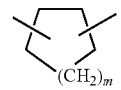

in which m is an integer from 1 to 4.

38. A method according to claim 35 in which the compound has the Structure IA1:
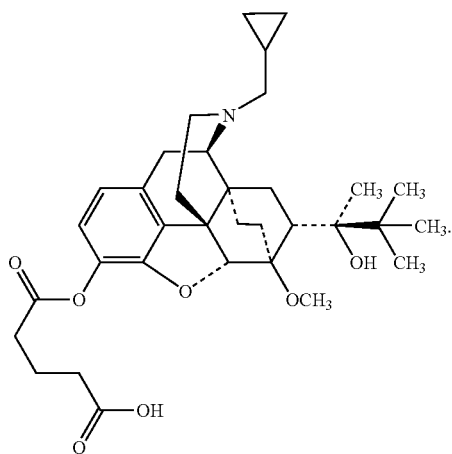
39. A method according to claim 35 in which the compound has the structure IA2:
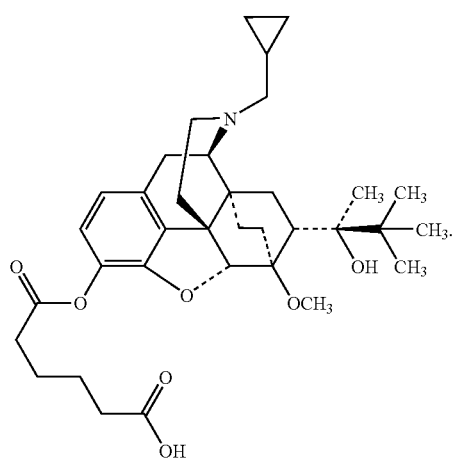
* * * * *